(12) United States Patent
Kumagai et al.

(10) Patent No.: US 7,964,709 B2
(45) Date of Patent: Jun. 21, 2011

(54) MUTANT TYROSINE REPRESSOR, A GENE ENCODING THE SAME, AND A METHOD FOR PRODUCING L-DOPA

(75) Inventors: Hidehiko Kumagai, Otsu (JP); Hideyuki Suzuki, Kyoto (JP); Takane Katayama, Kyoto (JP); Miyoko Nawata, Kawasaki (JP); Hidetsugu Nakazawa, Yokohama (JP)

(73) Assignee: Ajinomoto Co., Inc., Tokyo (JP)

( * ) Notice: Subject to any disclaimer, the term of this patent is extended or adjusted under 35 U.S.C. 154(b) by 501 days.

(21) Appl. No.: 11/855,256

(22) Filed: Sep. 14, 2007

(65) Prior Publication Data

US 2009/0258400 A1    Oct. 15, 2009

Related U.S. Application Data

(63) Continuation of application No. 11/091,914, filed on Mar. 29, 2005, now Pat. No. 7,365,161.

(30) Foreign Application Priority Data

Mar. 29, 2004    (JP) .................................. 2004-095147

(51) Int. Cl.
*C07H 21/02* (2006.01)
*C12P 1/00* (2006.01)
(52) U.S. Cl. ........................................ 536/23.1; 435/41
(58) Field of Classification Search .................. None
See application file for complete search history.

(56) References Cited

U.S. PATENT DOCUMENTS 6,146,878 A    11/2000    Kumagai et al.

FOREIGN PATENT DOCUMENTS

JP    2001-238678    9/2001

OTHER PUBLICATIONS

Definition of revertant (last viewed on Feb. 23, 2010).*
NCBI Taxonomy Brower—Pantoea agglomerans (last viewed on Feb. 23, 2010).*
Hybridization condition to % identity (last viewed on Feb. 24, 2010).*
GC content calculation (last viewed on Feb. 24, 2010).*
Kumagai, H., et al., "High-level expression of tyrosine phenol-lyase by mutation of the transcriptional regulator TyrR," Vitamin B Research Committee, The 376th Conference, Abstract of Research Reports, 2000, p. 386, with English translation thereof.
Notice of Reason for Rejection for Japanese Patent App. No. 2004-095147 (Nov. 17, 2009) with English translation thereof.
Cornish, E. C., et al., "Structure of the *Escherichia coli* K12 Regulatory gene *tyrR*," J. Biol. Chem. 1986;261(1):403-410.

(Continued)

*Primary Examiner* — Alexander D Kim
(74) *Attorney, Agent, or Firm* — Shelly Guest Cermak; Cermak Nakajima LLP

(57) ABSTRACT

A mutant tyrosine repressor that does not require tyrosine to induce expression of tyrosine phenol-lyase gene is obtained by introducing a mutation into a tyrosine repressor. A microorganism which is able to express large amounts of tyrosine phenol-lyase is obtained by introducing the mutant tyrosine repressor into the microorganism. The microorganism is useful for producing L-DOPA.

16 Claims, 9 Drawing Sheets

OTHER PUBLICATIONS

Katayama, T., et al., "Cloning and Random Mutagenesis of the *Erwinia herbicola tyrR* Gene for High-Level Expression of Tyrosine Phenol-Lyase," App. Environmen. Microbiol. 2000;66(11):4764-4771.

Koyanagi, T., et al., "Effective production of 3,4-dihydroxyphenyl-L-alanine (L-DOPA) with *Erwinia herbicola* cells carrying a mutant transcriptional regulator TyrR," J. Biotechnol. 2005;115:303-306.

Smith, H. Q., et al., "The *tpl* Promoter of *Citrobacter freundii* Is Activated by the TyrR Protein," J. Bacteriol. 1997;179(18):5914-5921.

Yang, J., et al., "Mutations in the *tyrR* Gene of *Escherichia coli* Which Affect TyrR-Mediated Activation but Not TyrR-Mediated Repression," J. Bacteriol. 1993;175(19):6372-6375.

Search Report for EP Patent App. No. 05006830.3 (Jul. 8, 2005).

* cited by examiner

SEQUENCE LISTING

```
<160> NUMBER OF SEQ ID NOS: 3

<210> SEQ ID NO 1
<211> LENGTH: 3363
<212> TYPE: DNA
<213> ORGANISM: Pantoea agglomerans
<220> FEATURE:
<221> NAME/KEY: CDS
<222> LOCATION: (442)..(2004)

<400> SEQUENCE: 1
gtcgacgcgt gccgcagggc attggtgcgg ggctgctcac cgcccggctg ggtatcaaag       60
cgatggagct gtgtcggcct ttaccctggc tggaaaatga taaacctcgt ctcggcgatt      120
accgcgggag ctgttagggc agttgaaaga cgcgctacaa aagggcggga ataaacatcc      180
acaaaactga ctttagatgg ggccgttatt taacgtcccc tgtttagcgc gccaaatctg      240
cgggggaccg ttccgggata ctgggaagat taactgcgaa agacgtcgaa aactcaaggt      300
gttatggcgc gctgcgcgcg acggacgttt aaaaaaaacg cgcttgcgtt aacgctgtca      360
acttttcctg acagccccct ttctgcggac gggctgttta gcgtattatc gcgacatatc      420
aaacggatta aggcccacgc a atg cgt tta gaa gtg ttt tgt cag gac cgt       471
                          Met Arg Leu Glu Val Phe Cys Gln Asp Arg
                          1               5                   10 atc gga ctg gcg cgt gaa ttg ctc gac ctg ttg gtg gcg cgt agt atc       519
Ile Gly Leu Ala Arg Glu Leu Leu Asp Leu Leu Val Ala Arg Ser Ile
                15                  20                  25 gat ctc cgc ggc att gaa gtc gcc gcc tca ggc cgt atc tat ctt aat       567
Asp Leu Arg Gly Ile Glu Val Ala Ala Ser Gly Arg Ile Tyr Leu Asn
```

```
                30              35              40
ttc tcc acg ctt gaa ttc gaa cag ttc agt aat ctg atg gcg gaa atc    615
Phe Ser Thr Leu Glu Phe Glu Gln Phe Ser Asn Leu Met Ala Glu Ile
         45                  50                  55 cgt cgt aca ccc ggc gtc acc gat gtc cgc acg gtc ccc tat atg ccg    663
Arg Arg Thr Pro Gly Val Thr Asp Val Arg Thr Val Pro Tyr Met Pro
 60                  65                  70 tct gaa cgt gaa cat cgg gta ctc agc gcc ttg ctg gtt gcc atg cca    711
Ser Glu Arg Glu His Arg Val Leu Ser Ala Leu Leu Val Ala Met Pro
 75                  80                  85                  90 gag ccg gta ttt tcg gtt gat ttg aga acg aag gtt gag ctg gcg aac    759
Glu Pro Val Phe Ser Val Asp Leu Arg Thr Lys Val Glu Leu Ala Asn
             95                 100                 105 ccg gcg gcg caa aac ctg ttt aat ctt gat gaa aac aag atc cgc aat    807
Pro Ala Ala Gln Asn Leu Phe Asn Leu Asp Glu Asn Lys Ile Arg Asn
        110                 115                 120 ttt acc gcc gac cac ctg att aac ggt ttt aat ttt gcg cgt tgg ctg    855
Phe Thr Ala Asp His Leu Ile Asn Gly Phe Asn Phe Ala Arg Trp Leu
                125                 130                 135 gag agc gaa cgc gtt cag gcg cag gcg caa cat gtg gtg ata gaa ggg    903
Glu Ser Glu Arg Val Gln Ala Gln Ala Gln His Val Val Ile Glu Gly
    140                 145                 150 cgc gac ttc ctg atg gaa gca cac ccg att tac ctg tca gag gac aac    951
Arg Asp Phe Leu Met Glu Ala His Pro Ile Tyr Leu Ser Glu Asp Asn
155                 160                 165                 170 gac cag gcc gac cag ctc gtc ggc gca atg gtg atg ctg aag tct act    999
Asp Gln Ala Asp Gln Leu Val Gly Ala Met Val Met Leu Lys Ser Thr
            175                 180                 185 gcc cgt atg ggg cga caa ctg cag aac ctg gtg gtg acc gat gaa acc   1047
Ala Arg Met Gly Arg Gln Leu Gln Asn Leu Val Val Thr Asp Glu Thr
        190                 195                 200 gag ttc gat cat att gtc gcc gtt acg ccc agg atg cgg cag gtc gtg   1095
Glu Phe Asp His Ile Val Ala Val Thr Pro Arg Met Arg Gln Val Val
                205                 210                 215 gaa cag gcg cgc aag ctc gcg atg cac gat gca ccg ctg ctg att atc   1143
Glu Gln Ala Arg Lys Leu Ala Met His Asp Ala Pro Leu Leu Ile Ile
    220                 225                 230 ggc gac acc ggc acg ggc aaa gac atg ctg gcg cgg gcc tgt cat tta   1191
Gly Asp Thr Gly Thr Gly Lys Asp Met Leu Ala Arg Ala Cys His Leu
235                 240                 245                 250 cgc agc gca cgc gga aag atg cct ttt ctg gcg ctt aac tgt gca tcg   1239
Arg Ser Ala Arg Gly Lys Met Pro Phe Leu Ala Leu Asn Cys Ala Ser
            255                 260                 265 ctg ccg gat gac gta gcg gaa agt gag ctt ttt ggt cac gca gcc ggg   1287
Leu Pro Asp Asp Val Ala Glu Ser Glu Leu Phe Gly His Ala Ala Gly
        270                 275                 280 gcc tat ccc aat gcg ctg gag ggc aaa aaa ggc ttt ttc gaa cag gca   1335
Ala Tyr Pro Asn Ala Leu Glu Gly Lys Lys Gly Phe Phe Glu Gln Ala
                285                 290                 295 aac ggt ggc tcg gtg ctg ctg gat gaa att ggc gag atg tca ccc act   1383
Asn Gly Gly Ser Val Leu Leu Asp Glu Ile Gly Glu Met Ser Pro Thr
    300                 305                 310 atg cag acg aag ctg ctg cgt ttt ctg aac gat ggc act ttc cgc cgc   1431
Met Gln Thr Lys Leu Leu Arg Phe Leu Asn Asp Gly Thr Phe Arg Arg
315                 320                 325                 330 gtc ggt gag gag cat gag gta cac gtg aat gtc cgc gtg atc tgc gcc   1479
Val Gly Glu Glu His Glu Val His Val Asn Val Arg Val Ile Cys Ala
            335                 340                 345 acc cag aag aac ctg ttt gag ctg gtt cag cgc ggc gag ttc agg gaa   1527
Thr Gln Lys Asn Leu Phe Glu Leu Val Gln Arg Gly Glu Phe Arg Glu
```

```
                         350                 355                 360
gac ctt ttc tat cgc ctg aat gtg ctt acg ctg aat ctg ccg ccg ctg    1575
Asp Leu Phe Tyr Arg Leu Asn Val Leu Thr Leu Asn Leu Pro Pro Leu
        365                 370                 375 cgc gag cgc gtt cag gac att atg ccg ctg acg gaa att ttc gtg gcg    1623
Arg Glu Arg Val Gln Asp Ile Met Pro Leu Thr Glu Ile Phe Val Ala
    380                 385                 390 cgt ttc gcc gat gaa cag ggc att cct cgg ccg cgt ctt tcc tca cag    1671
Arg Phe Ala Asp Glu Gln Gly Ile Pro Arg Pro Arg Leu Ser Ser Gln
395                 400                 405                 410 ctg aat gct ttt ctg atg cgc tat aac tgg ccc gga aac gtg cgg cag    1719
Leu Asn Ala Phe Leu Met Arg Tyr Asn Trp Pro Gly Asn Val Arg Gln
                415                 420                 425 ctt aaa aat gcc ttg tat cgt gca tta acc cag ttg gaa ggc cat gag    1767
Leu Lys Asn Ala Leu Tyr Arg Ala Leu Thr Gln Leu Glu Gly His Glu
            430                 435                 440 tta cgg ccg cag gat atc gtc ttg ccg gaa cag gcg ctg gat gtg tca    1815
Leu Arg Pro Gln Asp Ile Val Leu Pro Glu Gln Ala Leu Asp Val Ser
        445                 450                 455 ctg ggg gaa gaa gcg atg gaa ggc acg ctg gat cag atc acc agc cgc    1863
Leu Gly Glu Glu Ala Met Glu Gly Thr Leu Asp Gln Ile Thr Ser Arg
    460                 465                 470 ttt gaa cga tct att ttg acg cgg tta tat ttg tct tat ccg agc acg    1911
Phe Glu Arg Ser Ile Leu Thr Arg Leu Tyr Leu Ser Tyr Pro Ser Thr
475                 480                 485                 490 cgc aaa ctg gca aaa cga ctg ggg gtt tcc cat acc gcc att gcc aat    1959
Arg Lys Leu Ala Lys Arg Leu Gly Val Ser His Thr Ala Ile Ala Asn
                495                 500                 505 aaa ctg cgt gag tac ggt ctg ggg cag aag cgc ggc gac aac gaa        2004
Lys Leu Arg Glu Tyr Gly Leu Gly Gln Lys Arg Gly Asp Asn Glu
            510                 515                 520 taaaacgcag cggataagtc tggcttatcc gctgtggcca ttatttcagc gcagcgagtg  2064
cggcatcata atcgggttca gtggtgatct cattcaccag ctggctgtaa agcactttgt  2124
catgctcatc cagtacgata acggcacggg ccgtcagacc ctgaagggca ccatcagcaa  2184
tttccacgcc aaaatctttt ttgaattccc cgccgcgcag cgttgacagc gtaaccacgt  2244
tgttgaggtt gtctgcgcca caaaaacgcg attgagcaaa gggcaggtcg gcggaaatac  2304
ataacaccac cgtgttattc agttcgcccg ctaactggtt aaacttgcgc accgaagagg  2364
cgcacacgcc ggtatcgacg ctgggaaaaa tattcagaat cttgcgtttt cctgcatact  2424
cagagagtga aacgttagac aggttttttcg ccacgagggt aaaagcgtta acgctatcgc  2484
ccggctgcgg gaactgacct gcaaccgcta cagggttgcc ctgaaagtga acagtctgag  2544
acataagaat tccttctaat gatgttatct gacagaaaag aaagcgtcag tacaggtata  2604
gccattgttt atgacataaa ttttaagggt ttacgagagc atttgttgcc taaagttaaa  2664
tggcgatgat gaatcccaga gaaaggaga ggtaatgaga acggtaaaat gttatcccga  2724
agcatggccg ctgcatacgc cgtttgtcat tgctcgtggc agtcgcaccg aagccaaggt  2784
cgttgtcgtc gaaatcgaag aagagggcgt gaaaggatc ggcgaggcca cgccttacac  2844
gcgctacggc gaaagcgaag ccctggtgct ggaacaaatt gcgaccgtta tgcctcaact  2904
gcagcaaggg ctgtcgcgtg aagccttgca gagcctgttg cctgccggtg cggcaagaaa  2964
cgccatcgac agtgctctct gggaccttgc cgctcgccag cagcatgtga cgctggagca  3024
gttagtgggc gcggaaccga cccagtctgt tgtgactgca cacacggtga gcattgatac  3084
gccggaagcg atggccagca gcgcgcaggc gttgtggcaa catggcgcaa cactgctcaa  3144
```

```
aatcaaaatg gacaataact ttattaccga gcgcctgatg gcgattcgcg ctgctgttcc    3204
cgacgcgaca ttacttgtgg atgcgaatga atcctggcat gccgaaggct ggcagcccgt    3264
tgccagctgt tagccgatct ggaggtggcc atgctggaac agccgttacc ggcaggtgaa    3324
gacgcggcgc tggcgaactt tatccatcct cttccgatc                           3363
```

<210> SEQ ID NO 2
<211> LENGTH: 521
<212> TYPE: PRT
<213> ORGANISM: Pantoea agglomerans

<400> SEQUENCE: 2

```
Met Arg Leu Glu Val Phe Cys Gln Asp Arg Ile Gly Leu Ala Arg Glu
1               5                   10                  15

Leu Leu Asp Leu Val Ala Arg Ser Ile Asp Leu Arg Gly Ile Glu
            20                  25                  30

Val Ala Ala Ser Gly Arg Ile Tyr Leu Asn Phe Ser Thr Leu Glu Phe
        35                  40                  45

Glu Gln Phe Ser Asn Leu Met Ala Glu Ile Arg Arg Thr Pro Gly Val
    50                  55                  60

Thr Asp Val Arg Thr Val Pro Tyr Met Pro Ser Glu Arg Glu His Arg
65                  70                  75                  80

Val Leu Ser Ala Leu Leu Val Ala Met Pro Glu Pro Val Phe Ser Val
                85                  90                  95

Asp Leu Arg Thr Lys Val Glu Leu Ala Asn Pro Ala Ala Gln Asn Leu
            100                 105                 110

Phe Asn Leu Asp Glu Asn Lys Ile Arg Asn Phe Thr Ala Asp His Leu
        115                 120                 125

Ile Asn Gly Phe Asn Phe Ala Arg Trp Leu Glu Ser Glu Arg Val Gln
    130                 135                 140

Ala Gln Ala Gln His Val Val Ile Glu Gly Arg Asp Phe Leu Met Glu
145                 150                 155                 160

Ala His Pro Ile Tyr Leu Ser Glu Asp Asn Asp Gln Ala Asp Gln Leu
                165                 170                 175

Val Gly Ala Met Val Met Leu Lys Ser Thr Ala Arg Met Gly Arg Gln
            180                 185                 190

Leu Gln Asn Leu Val Val Thr Asp Glu Thr Glu Phe Asp His Ile Val
        195                 200                 205

Ala Val Thr Pro Arg Met Arg Gln Val Val Glu Gln Ala Arg Lys Leu
    210                 215                 220

Ala Met His Asp Ala Pro Leu Leu Ile Ile Gly Asp Thr Gly Thr Gly
225                 230                 235                 240

Lys Asp Met Leu Ala Arg Ala Cys His Leu Arg Ser Ala Arg Gly Lys
                245                 250                 255

Met Pro Phe Leu Ala Leu Asn Cys Ala Ser Leu Pro Asp Asp Val Ala
            260                 265                 270

Glu Ser Glu Leu Phe Gly His Ala Ala Gly Ala Tyr Pro Asn Ala Leu
        275                 280                 285

Glu Gly Lys Lys Gly Phe Phe Glu Gln Ala Asn Gly Gly Ser Val Leu
    290                 295                 300

Leu Asp Glu Ile Gly Glu Met Ser Pro Thr Met Gln Thr Lys Leu Leu
305                 310                 315                 320

Arg Phe Leu Asn Asp Gly Thr Phe Arg Arg Val Gly Glu Glu His Glu
                325                 330                 335

Val His Val Asn Val Arg Val Ile Cys Ala Thr Gln Lys Asn Leu Phe
```

```
                    340             345             350
Glu Leu Val Gln Arg Gly Glu Phe Arg Glu Asp Leu Phe Tyr Arg Leu
            355                 360                 365

Asn Val Leu Thr Leu Asn Leu Pro Pro Leu Arg Glu Arg Val Gln Asp
        370                 375                 380

Ile Met Pro Leu Thr Glu Ile Phe Val Ala Arg Phe Ala Asp Glu Gln
385                 390                 395                 400

Gly Ile Pro Arg Pro Arg Leu Ser Ser Gln Leu Asn Ala Phe Leu Met
                405                 410                 415

Arg Tyr Asn Trp Pro Gly Asn Val Arg Gln Leu Lys Asn Ala Leu Tyr
            420                 425                 430

Arg Ala Leu Thr Gln Leu Glu Gly His Glu Leu Arg Pro Gln Asp Ile
            435                 440                 445

Val Leu Pro Glu Gln Ala Leu Asp Val Ser Leu Gly Glu Glu Ala Met
        450                 455                 460

Glu Gly Thr Leu Asp Gln Ile Thr Ser Arg Phe Glu Arg Ser Ile Leu
465                 470                 475                 480

Thr Arg Leu Tyr Leu Ser Tyr Pro Ser Thr Arg Lys Leu Ala Lys Arg
                485                 490                 495

Leu Gly Val Ser His Thr Ala Ile Ala Asn Lys Leu Arg Glu Tyr Gly
            500                 505                 510

Leu Gly Gln Lys Arg Gly Asp Asn Glu
            515                 520

<210> SEQ ID NO 3
<211> LENGTH: 2378
<212> TYPE: DNA
<213> ORGANISM: Pantoea agglomelans

<400> SEQUENCE: 3
gatcaggggc atattccgct taagctgctt ggcttttacg acggggtgaa catcacggca      60
ggattgcctt tcctgcgtac ttcagccgat cacggtacgg catttaacat cgcctggaca     120
ggtaaggcta atccggagag tatggcgata tcaattgata tggccatgaa gattacccgg     180
gagtaataat ttatcgaaag ctaatgcttt ctggtcactc aggcgatggc aagacatccg     240
ttttctccac cgggctgaag cgtcatcgct gtccacaacc catccacctc aacacgttac     300
ctccacttcg cttgcaaatg actacgagca gatagtcatg ctctattaca taagttctct     360
ttatttaagt tttgatcggc agcgacctgc ctcagtggga taatatgaat ggattgtctc     420
agtgctgtag cgactttctt atttcacgtc attaacattc gccgctcagt taataactcg     480
gtgatgtaca ttgaagttta cggattttaa gcaaccgctg tgattattca ttttttatgt     540
gatcgctgcc tcatattatc tggttaaaaa tgtcacattt attaccaata agaaaatgg      600
aaagataagt tttcattgtt atcaaccttaa accgactttt ctgtttctgt atgaccgacg    660
gccgttacgc taacgctatg aatattcagc atacatggcc gatctttttt gatgtttaat     720
cattttacg ttttatacat tgtcagaaag gcgcgcatag tgacgcggct attttcatcg      780
catgataaat cccgcatgat ggtgtcgtat tatttccacc tcaattctga ggttattgtt     840
atatcttcct gtgcatttca tctatgcacc agacttattc gacgcgcatt tttctgcgta     900
tgaaaatgga taactggaga ataaacatg aactatcctg ccgagccttt ccgcattaaa      960
agtgttgaaa ccgtatcaat gatctcacgc gatgagcgtg ttaaaaaaat gcaagaagcg    1020
ggctataaca cgttttttact gaattcaaag gatatctaca tcgatctgct gacagacagc   1080
ggtacaaatg ccatgagtga caagcagtgg gcagggatga tgattggtga tgaagcctac   1140
```

```
gcaggcagtg aaaacttcta ccatctcgaa aaaacggtga aagagttgtt tggtttcaaa    1200
cacatcgttc caacccacca gggacgcggg gcggaaaacc tgctctcgca gctggccatt    1260
aagcccggtc aatatgtcgc aggaaatatg tactttacaa caacccgctt ccatcaggaa    1320
aaaaatggcg caacctttgt ggatattgtc cgcgatgaag cacatgacgc cagcctgaat    1380
ctccccttta aaggtgatat tgacctgaat aaattagcga cgctcattaa agaaaaaggc    1440
gccgagaaca tcgcctatat ctgccttgcg gtcaccgtga atctggcggg tgggcagcct    1500
gtttcaatgg cgaatatgcg tgccgtacat gaaatggcca gcacgtatgg cattaagatc    1560
ttttacgatg ccacccgttg cgttgaaaat gcctatttta tcaaagagca ggaagcgggc    1620
tacgagaacg tcagtatcaa agatatcgtg catgaaatgt tcagctatgc cgatgggtgc    1680
accatgagcg gtaaaaaaga ttgtctggtg aatatcggcg gcttcttgtg tatgaacgat    1740
gaggagatgt tctcagcggc aaaagagttg gttgtcgttt atgaaggtat gccgtcatac    1800
ggcgggctgg ccggtcggga tatggaagcg atggctattg ggctacgtga agccatgcag    1860
tatgaatata ttgaacatcg ggtcaaacag gtgcgctatc tgggcgataa actccgtgaa    1920
gccggcgtac ccattgttga accgacgggc ggacatgcgg tatttcttga tgctcgtcgt    1980
ttctgtccac acctgacgca ggatcagttc cctgcgcaga gcctggcagc cagcatctat    2040
atggaaaccg gcgtgcgaag tatggaacgt ggaattgttt ctgccggtcg tagcaaggaa    2100 acggggggaga accatcgccc caaactggag acggtacgtc tcactattcc acgccgtgtt    2160
tacacttacg cgcacatgga tgttgttgcc gatggcatca ttaaactgta ccagcataaa    2220
gaagatattc gtggtctgac gtttgtttat gaacctaaac aacttcgctt ctttactgcg    2280
cgttttgact ttatttaata caaccctggc gcaggggccc tgtttctctc ctatcgccct    2340
tcctttattt cagacctgcc gccatggcag gtctgcag                            2378
```

MUTANT TYROSINE REPRESSOR, A GENE ENCODING THE SAME, AND A METHOD FOR PRODUCING L-DOPA

This application claims priority under 35 U.S.C. §119 to Japanese Patent Application No. 2004-95147, filed Mar. 29, 2004, and under 35 U.S.C. §120 as a continuation to U.S. patent application Ser. No. 11/091,914, filed Mar. 29, 2005, now U.S. Pat. No. 7,365,161 the contents of both of which are incorporated by reference in their entireties. The Sequence Listing filed electronically herewith is also hereby incorporated by reference in its entirety (File Name: US-219C_Seq_List_Copy_1; File Size: 18 KB; Date Created: Sep. 13, 2007).

BACKGROUND OF THE INVENTION

1. Field of the Invention

The present invention relates to a mutant tyrosine repressor that does not require tyrosine to induce expression of a tyrosine phenol-lyase gene. The present invention also relates to a gene encoding the mutant tyrosine repressor, and utilization thereof. The mutant tyrosine repressor is useful in the field of fermentation, for example, in the production of L-3, 4-dihydroxyphenylalanine, hereinafter, "L-DOPA".

2. Brief Description of the Related Art

L-DOPA is a precursor of dopamine. Dopamine is a nerve transmitter and is useful as a therapeutic agent for Parkinson's disease, and so forth. L-DOPA has conventionally been manufactured by chemical synthesis. In recent years, however, L-DOPA is enzymatically synthesized from catechol and serine, or catechol, pyruvic acid, and ammonia using tyrosine phenol-lyase (TPL).

TPL is known to be produced by a wide variety of microorganisms, including those belonging to the genus *Escherichia, Pseudomonas, Flavobacterium, Bacillus, Serratia, Xanthomonas, Agrobacterium, Achromobacter, Aerobacter, Erwinia, Proteus, Salmonella, Citrobacter, Enterobacter, Pantoea*, or the like (Japanese Patent No. 2521945 or Japanese Patent Publication (Kokoku) No. 6-98003). Enzymatic characteristics of TPL have also been elucidated (Biochem. Biophys. Res. Commun., 33, 10 (1963)). Furthermore, nucleotide sequences of the structural gene and an upstream region of the TPL gene from *Erwinia* bacteria, which highly expresses TPL, have been reported (Suzuki, H. et al., J. Ferment. Bioeng., 75, No. 2, 145-148 (1993)).

It is known that expression of TPL is regulated by a tyrosine repressor. That is, the tyrosine repressor is activated when tyrosine binds to it, and thereby expression of the TPL gene is induced. The structure of the tyrosine repressor gene has been elucidated for *Escherichia coli* (Cornish, E. C. et al., J. Biol. Chem., 261, 403-410 (1986)). Furthermore, the inventors of the present invention successfully isolated a gene encoding a tyrosine repressor from *Erwinia* bacteria and reported that the tyrosine repressor has an activity of positively regulating expression of the TPL gene (U.S. Pat. No. 6,146,878).

Production of L-DOPA using microbial cells has also been attempted. To efficiently produce L-DOPA, it is important to use a microorganism which expresses a high amount of TPL. The addition of large amounts of tyrosine to a culture medium is required since tyrosine induces the expression of TPL. However, the extremely low solubility of tyrosine in water causes a large amount of tyrosine, which can contaminate the L-DOPA reaction system during cultivation, resulting in difficulty purifying and isolating L-DOPA. To solve this problem, a mutant tyrosine repressor that is able to express a high amount of TPL in the presence of small amounts of tyrosine has been developed (Japanese Patent Laid-open No. 2001-238678). However, this mutant expresses TPL more efficiently when tyrosine is added, and therefore development of a microorganism that expresses large amounts of TPL in the absence of tyrosine is desired.

The microorganisms disclosed as *Erwinia herbicola* in U.S. Pat. No. 6,146,878 and Japanese Patent Laid-open No. 2001-238678 and so forth have been reclassified into *Pantoea agglomerans*. Therefore, the aforementioned *Erwinia herbicola* will be referred to as *Pantoea agglomerans* hereinafter.

SUMMARY OF THE INVENTION

An object of the present invention is to provide a novel technique utilizing a mutant tyrosine repressor gene. Specifically, an object of the present invention is to provide a mutant tyrosine repressor that expresses a sufficient amount of a tyrosine phenol-lyase (TPL) gene in the absence of tyrosine, and to provide a gene encoding the same and a method of producing L-DOPA utilizing these.

The inventors of the present invention introduced various mutations into the tyrosine repressor gene and analyzed the activity of the obtained mutant tyrosine repressors. As a result, they found that, whereas a small amount of TPL gene was expressed by a wild-type tyrosine repressor in the absence of tyrosine, a sufficient amount of TPL was expressed by the mutant tyrosine repressor having replacements of the valine residue at position 67, the tyrosine residue at position 72, the glutamic acid residue at position 201, the asparagine residue at position 324, and so forth, even in the absence of tyrosine. Furthermore, they found that L-DOPA could be efficiently produced by using a microorganism having such a mutant tyrosine repressor, and thus accomplished the present invention.

That is, the present invention provides the following:

It is an object of the present invention to provide a mutant tyrosine repressor, wherein said mutant tyrosine repressor does not require tyrosine to induce expression of a tyrosine phenol-lyase gene.

It is an object of the present invention to provide mutant tyrosine repressor comprising a wild-type tyrosine repressor having mutations at positions of at least two of the following (a) to (c):

(a) position 67, position 72, and position 201, (b) position 324, and (c) position 503.

It is a further object of the present invention to provide the mutant tyrosine repressor as described above, wherein said mutation at position 67 is an alanine, said mutation at position 72 is a cysteine, said mutation at position 201 is a glycine, said mutation at position 324 is an aspartic acid, and said mutation at position 503 is a threonine.

It is a further object of the present invention to provide the mutant tyrosine repressor as described above, wherein said mutant tyrosine repressor includes substitution, deletion, insertion, addition or inversion of one or several amino acid residues at a position other than the positions listed in (a), (b), or (c) above, and wherein said mutant tyrosine repressor does not require tyrosine to induce expression of a tyrosine phenol-lyase gene.

It is a further object of the present invention to provide the mutant tyrosine repressor as described above, wherein said wild-type tyrosine repressor is a wild-type *Pantoea agglomerans* tyrosine repressor.

It is a further object of the present invention to provide the mutant tyrosine repressor as described above comprising an amino acid sequence of SEQ ID NO: 2.

It is a further object of the present invention to provide a DNA encoding said mutant tyrosine repressor as described above.

It is a further object of the present invention to provide an *Escherichia* or *Pantoea* bacterium which is transformed with said DNA as described above.

It is a further object of the present invention to provide the *Escherichia* or *Pantoea* bacterium as described above, further comprising a structural gene operably linked to a tyrosine phenol-lyase gene promoter.

It is a further object of the present invention to provide a method for producing tyrosine phenol-lyase comprising (a) culturing said *Escherichia* or *Pantoea* bacterium as described above in a medium, and (b) collecting said tyrosine phenol-lyase.

It is a further object of the present invention to provide the method for producing tyrosine phenol-lyase as described above, wherein said bacterium is cultured in the absence of tyrosine.

It is a further object of the present invention to provide a method for producing L-3,4-dihydroxyphenylalanine comprising (a) allowing the *Escherichia* or *Pantoea* bacterium as described above to act on a mixture selected from the group consisting of (1) catechol, pyruvic acid and ammonia, and (2) catechol and serine and (b) collecting said L-3,4-dihydroxyphenylalanine.

It is a further object of the present invention to provide the method for producing L-3,4-dihydroxyphenylalanine as described above, wherein said bacterium is grown in the absence of tyrosine.

In the present specification, a tyrosine repressor having the aforementioned mutations may be referred to as a "mutant tyrosine repressor," and a DNA encoding such a mutant tyrosine repressor may be referred to as a "mutant tyrosine repressor gene." Furthermore, a tyrosine repressor not having the aforementioned mutations may be referred to as a "wild-type tyrosine repressor." Tyrosine repressor may be referred to as "TyrR".

DESCRIPTION OF THE PREFERRED EMBODIMENTS

Figure 1:
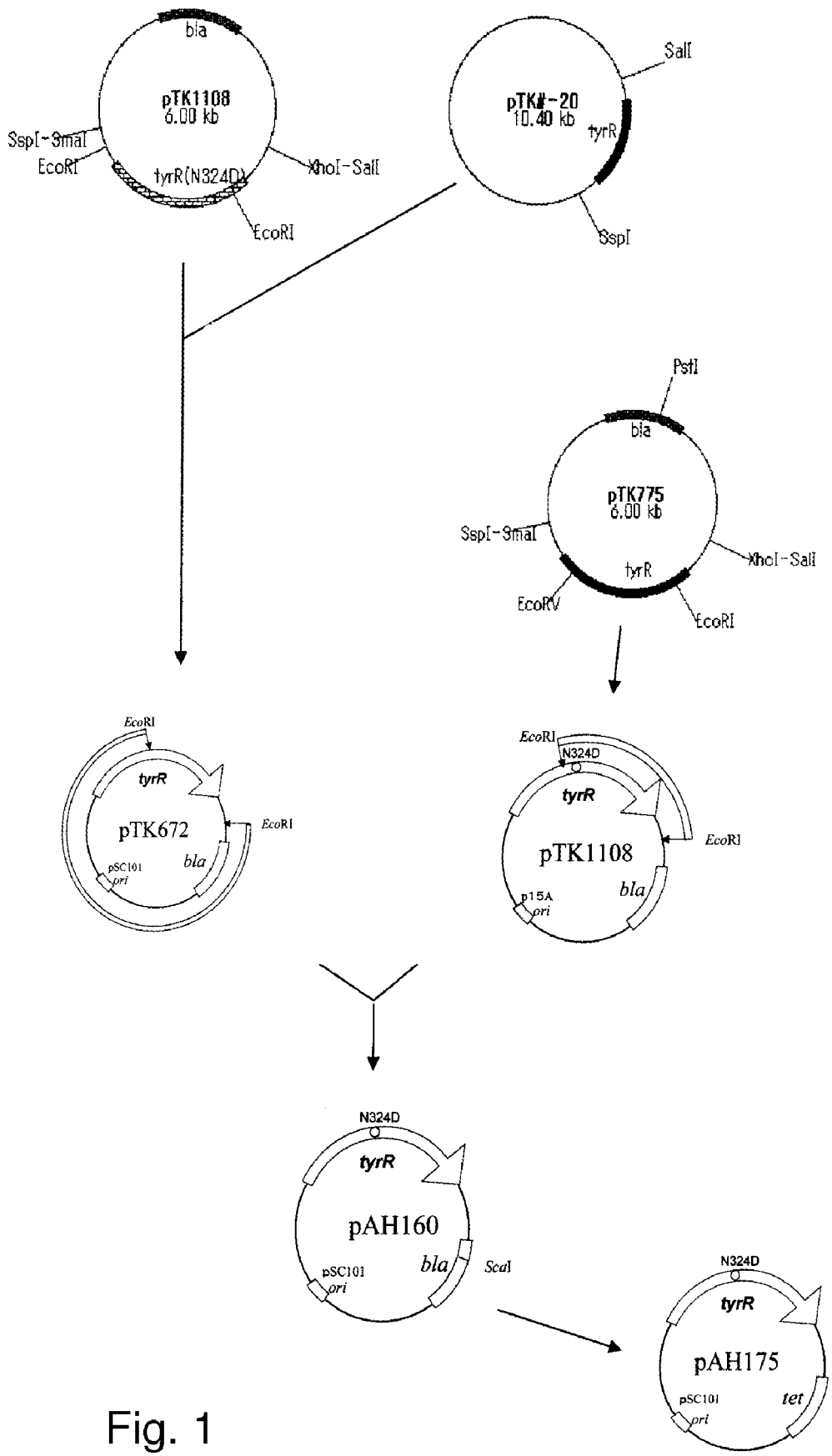
FIG. 1 shows the construction procedure for the plasmid pAH175.

Hereinafter, the present invention will be explained in detail.

The mutant tyrosine repressor (TyrR) of the present invention has the amino acid sequence of a wild-type tyrosine repressor except that one or several amino acid residues are replaced, and the mutant repressor does not require tyrosine to induce expression of tyrosine phenol-lyase (TPL) gene. The term "several" used herein means preferably 2 to 20, more preferably 2 to 10, particularly preferably 2 to 5 amino acids. Furthermore, the phrase "does not require tyrosine to induce expression of tyrosine phenol-lyase (TPL) gene" means that expression of the TPL gene occurs in the absence of tyrosine, or the expression level of the TPL gene occurs at a minimum value comparable to or higher than the expression level in the presence of sufficient tyrosine usually required to induce expression of the TPL gene (e.g., 0.2%). The term "minimum value" used herein refers to, for example, a concentration of 0.01% or lower, preferably $3.0 \times 10^{-3}$% or lower.

Furthermore, the phrase "comparable to or higher than" means that an expression level in the absence of tyrosine, or at a minimum value is preferably 60% or more, more preferably 80% or more, particularly preferably 100% of an expression level usually required with tyrosine present to induce expression of TPL gene. The ability of a mutant tyrosine repressor to induce expression of the TPL gene can be determined by, for example, expressing a mutant tyrosine repressor gene in a cell which expresses the TPL gene, quantifying, and comparing the amount of mRNA of TPL in the absence of tyrosine or a minimum value as well as a typical tyrosine concentration. The ability to induce expression can also be indirectly examined by determining the TPL activity of the cell transformed with a mutant tyrosine repressor. The TPL activity can be determined by, for example, measuring absorbance at 370 nm of a reaction solution containing a synthesized substrate as shown in the Examples.

The mutant tyrosine repressor of the present invention is not particularly limited so long as it does not require tyrosine to induce expression of the TPL gene, and specific examples thereof include a mutant tyrosine repressor having an amino acid sequence of the wild-type tyrosine repressor except that at least two of the following (a), (b), or (c) amino acid mutations are present at the following positions:
(a) position 67, position 72, and position 201
(b) position 324
(c) position 503.

That is, examples of the mutant tyrosine repressor of the present invention include (1) a mutant tyrosine repressor having an amino acid sequence in which the valine residue at position 67, the tyrosine residue at position 72, the glutamic acid residue at position 201, and the asparagine residue at position 324 are replaced with other amino acids, (2) a mutant tyrosine repressor having an amino acid sequence in which the valine residue at position 67, the tyrosine residue at position 72, the glutamic acid residue at position 201, and the alanine residue at position 503 are replaced with other amino acids, (3) a mutant tyrosine repressor having an amino acid sequence in which the valine residue at position 67, the tyrosine residue at position 72, the glutamic acid residue at position 201, the asparagine residue at position 324, and the alanine residue at position 503 are replaced with other amino acids, and (4) a mutant tyrosine repressor having an amino acid sequence in which the asparagine residue at position 324 and the alanine residue at position 503 are replaced with other amino acids.

Amino acids which replace the native amino acid residues at the aforementioned positions are not particularly limited so long as a mutant tyrosine repressor having such replacements does not require tyrosine to induce expression of the TPL gene. However, it is preferred that the valine residue at position 67 is replaced with alanine, the tyrosine residue at position 72 is replaced with cysteine, the glutamic acid residue at position 201 is replaced with glycine, the asparagine residue at position 324 is replaced with aspartic acid, and the alanine residue at position 503 is replaced with threonine.

In the present invention, examples of the wild-type tyrosine repressor include a tyrosine repressor from *Pantoea agglomerans*. The tyrosine repressor from *Pantoea agglomerans* may be a tyrosine repressor from a microorganism previously classified as *Erwinia herbicola*. As a wild-type tyrosine repressor from *Pantoea agglomerans*, a protein having the amino acid sequence shown in SEQ ID NO: 2 is preferred.

The mutant tyrosine repressor as mentioned above can be obtained by introducing a mutation that causes the aforementioned amino acid replacements into a DNA encoding a wild-type tyrosine repressor. The mutations can be introduced into target positions by site-directed mutagenesis or the like.

As the DNA encoding a wild-type tyrosine repressor, for example, a DNA encoding a wild-type tyrosine repressor from *Pantoea agglomerans* having the nucleotide sequence shown in SEQ ID NO: 1 can be used. For example, the DNA can be obtained by PCR using oligonucleotides based on the nucleotide sequence of SEQ ID NO: 1 from a chromosomal DNA or genomic DNA library of *Pantoea agglomerans*, or by hybridization using a probe having a partial sequence of SEQ ID NO: 1.

As described above, some microorganisms once classified as *Erwinia herbicola* have been reclassified into *Pantoea agglomerans*. Thus, the genus *Erwinia* is very closely related to the genus *Pantoea*, and therefore the tyrosine repressor gene may be obtained from a microorganism belonging to either the genus *Erwinia* or *Pantoea*. Furthermore, a tyrosine repressor gene may be obtained from bacteria belonging to a genus other than *Erwinia* or *Pantoea*, for example, *Escherichia* bacteria such as *Escherichia coli*, in the same manner as described above.

The mutant tyrosine repressor of the present invention may be a mutant tyrosine repressor having an amino acid sequence which includes substitution, deletion, insertion, addition or inversion of one or several amino acid residues at position(s) other than the aforementioned positions so long as tyrosine is not required to induce expression of the TPL gene. Although the number represented by the term "several" as used herein may differ depending on the position and type of amino acid residue in the three-dimensional structure of the protein, it is preferably 2 to 20, more preferably 2 to 10, and particularly preferably 2 to 5.

Substitution of amino acids is preferably a conserved substitution including substitution of ser or thr for ala, substitution of gln, his or lys for arg, substitution of glu, gln, lys, his or asp for asn, substitution of asn, glu or gln for asp, substitution of ser or ala for cys, substitution of asn, glu, lys, his, asp or arg for gln, substitution of gly, asn, gln, lys or asp for glu, substitution of pro for gly, substitution of asn, lys, gln, arg or tyr for his, substitution of leu, met, val or phe for ile, substitution of ile, met, val or phe for leu, substitution of asn, glu, gln, his or arg for lys, substitution of ile, leu, val or phe for met, substitution of trp, tyr, met, ile or leu for phe, substitution of thr or ala for ser, substitution of ser or ala for thr, substitution of phe or tyr for trp, substitution of his, phe or trp for tyr and substitution of met, ile or leu for val.

Furthermore, the mutant tyrosine repressor of the present invention may include the amino acid replacements in the aforementioned positions while having a homology of 80% or more, preferably 90% or more, particularly preferably 95% or more to the whole amino acid sequence of SEQ ID NO: 2, so long as tyrosine is not required to induce expression of the TPL gene. Homology of the amino acid sequences can be determined using the algorithm BLAST (Pro. Natl. Acad. Sci. USA, 90, and 5873 (1993)) and FASTA (Methods Enzymol., 183, and 63 (1990)) by Karlin and Altschul. The BLASTN and BLASTX programs have been developed based on the algorithm BLAST. (refer to http://www.ncbi.nlm.nih.gov).

The valine residue at position 67, the tyrosine residue at position 72, the glutamic acid residue at position 201, the asparagine residue at position 324 and the alanine residue at position 503 represent the positions in the amino acid sequence of the wild-type tyrosine repressor shown in SEQ ID NO: 2. These positions may be shifted ahead or backward by the aforementioned deletion, insertion, addition or inversion of one or several amino acids. For example, if one amino acid residue is inserted into the upstream position, the valine residue originally located at the position 67 shifts to position 68. A DNA encoding a protein substantially identical to the aforementioned mutant tyrosine repressor can be obtained by mutating the nucleotide sequence of the mutant tyrosine repressor gene, for example, with site-directed mutagenesis so that the amino acid sequence of the protein encoded by the nucleotide sequence contains substitution, deletion, insertion, addition or inversion of one or several amino acid residues at positions other than the aforementioned positions.

The aforementioned mutated gene can also be obtained by a conventionally known mutagenesis treatment. Examples of mutagenesis treatments include treating a DNA encoding a mutant tyrosine repressor in vitro with hydroxylamine or the like, irradiating a microorganism such as *Pantoea* bacteria harboring a DNA encoding a mutant tyrosine repressor with ultraviolet rays, or treating such a microorganism with a mutagenesis agent typically used in mutation treatments such as N-methyl-N'-nitro-N-nitrosoguanidine (NTG) and nitrous acid and so forth. Furthermore, the aforementioned DNA can be obtained by the error-prone PCR disclosed in Japanese Patent Laid-open No. 2001-238678.

Furthermore, the mutations causing substitution, deletion, insertion, addition or inversion of amino acid residues other than the aforementioned positions may be naturally occurring mutations which occur due to differences of genera or species or individual differences of strains of the microorganism harboring a tyrosine repressor (mutant or variant).

A DNA encoding a protein which is substantially identical to the mutant tyrosine repressor and does not require tyrosine to induce expression of the TPL gene can be selected by expressing a mutated DNA in an appropriate cell and examining the expression product tyrosine repressor activity, for example, positive regulation of expression of the TPL gene.

The DNA encoding a mutant tyrosine repressor of the present invention may encode a mutant tyrosine repressor having the amino acid replacements in the aforementioned positions and which hybridizes to a DNA having a nucleotide sequence of the numbers 442 to 2004 in the SEQ ID NO: 1 under stringent conditions, so long as the repressor encoded by the DNA does not require tyrosine to induce expression of the TPL gene. The term "stringent condition" used herein refers those under which a so-called specific hybrid is formed, but a nonspecific hybrid is not formed. Although it is difficult to numerically define this condition, examples thereof include washing one time, preferably two or three times, at salt concentrations of 1×SSC, 0.1% SDS at 65° C., preferably 0.1×SSC, 0.1% SDS at 65° C.

Although the DNAs hybridizing under such conditions include a DNA in which a stop codon has been generated, and a DNA which encodes a protein having a reduced or lost activity due to a mutation at the active site, these DNAs can be readily removed by expressing them in a host cell by using a commercially available expression vector and investigating the tyrosine repressor activity of the expression products.

A microorganism introduced with the mutant tyrosine repressor of the present invention can be suitably used for production of a recombinant TPL and production of substances such as L-DOPA. The host microorganism to be transformed with the mutant tyrosine repressor is not particularly limited so long as it expresses the TPL gene. The host microorganism may be a microorganism which inherently expresses the TPL gene, or which has the TPL gene exogenously introduced. The host microorganism may have an inherent tyrR gene disrupted. Examples of the host microorganism to be transformed with the mutant tyrosine repressor include *Escherichia* bacteria, *Pantoea* bacteria, and so forth. Examples of the *Escherichia* bacteria include, but are not limited to, *Escherichia coli*, and examples of the *Pantoea* bacteria include, but are not limited to, *Pantoea agglomerans* and *Pantoea ananatis*. The aforementioned *Pantoea* bacteria also include microorganisms which were previously classified as *Erwinia* bacteria such as *Erwinia herbicola* and have been reclassified as *Pantoea* bacteria.

For transformation of the aforementioned mutant tyrosine repressor gene into a microorganism such as *Escherichia* bacteria or *Pantoea* bacteria, a recombinant DNA is usually prepared by ligating the gene to a suitable vector. Examples of such a vector include pUC19, pUC18, pBR322, pHSG299, pHSG399, pHSG398, RSF1010, pACYC177, pACYC184, pMW219, pMW118, and so forth.

The recombinant DNA prepared as described above can be transformed into an *Escherichia* or *Pantoea* bacterium by known transformation methods. Examples of such transformation methods include treating recipient cells with calcium chloride so as to increase permeability of the DNA, which has been reported for *Escherichia coli* K-12 (Mandel, M. and Higa, A., J. Mol. Biol., 53, 159 (1970)), preparing competent cells from cells which are at the growth phase, followed by transformation with DNA, which has been reported for *Bacillus subtilis* (Duncan, C. H., Wilson, G. A. and Young, F. E., Gene, 1, 153 (1977)), and so forth. In addition to these methods, introducing a recombinant DNA into protoplast- or spheroplast-like recipient cells, which have been reported to be applicable to *Bacillus subtilis*, actinomycetes, and yeasts (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)), can be employed. In addition, transformation of microorganisms can also be performed by the electric pulse method (JP2-207791A).

The aforementioned mutant tyrosine repressor gene may also be integrated into the chromosomal DNA of the host microorganism. Homologous recombination (Experiments in Molecular Genetics, Cold Spring Harbor Lab., 1972) may be used for this purpose, and may be carried out by targeting a sequence which exists in multiple copies on the chromosomal DNA. Repetitive DNA and inverted repeats at an end of a transposon are typically used for this purpose. Alternatively, as disclosed in EP0332488B, it is also possible to incorporate a target gene into a transposon, and allow it to be transferred so that multiple copies of the gene are integrated into the chromosomal DNA. Furthermore, a target gene may also be incorporated into the host chromosome by using Mu phage (EP0332488B).

Expression of the mutant tyrosine repressor gene which has been introduced may be controlled by an inherent promoter of the tyrosine repressor gene. Alternatively, the promoter may be replaced with a stronger promoter such as the lac promoter, trp promoter, trc promoter, tac promoter, $P_R$ promoter or $P_L$ promoter of lambda phage, tet promoter, and amyE promoter.

As methods for preparation of chromosomal DNA, preparation of chromosomal DNA library, hybridization, PCR, preparation of plasmid DNA, digestion and ligation of DNA, transformation, design of oligonucleotides used as primers and so forth, ordinary methods known to those skilled in the art can be employed. These methods are described in Sambrook, J., Fritsch, E. F. and Maniatis, T., "Molecular Cloning A Laboratory Manual, Second Edition", Cold Spring Harbor Laboratory Press, (1989), and so forth.

A recombinant TPL can be produced by, for example, culturing a microorganism having a gene encoding a mutant tyrosine repressor and a TPL gene in a medium and collecting TPL from the culture or cells. Although the type of culture medium is not particularly limited, so long as the chosen microorganism can grow and produce TPL in the medium, such a medium as shown in the examples can be preferably used. A recombinant TPL may be produced as a fusion protein having a peptide tag for purification. Furthermore, a recombinant TPL is preferably produced in the absence of tyrosine. In the present invention, the phrase "in the absence of tyrosine" includes culture conditions where tyrosine does not exist at all and conditions where tyrosine does not substantially exist. Specific examples of the culture conditions where tyrosine does not substantially exist include a condition whereby the tyrosine concentration is 0.01% or lower, preferably $3.0 \times 10^{-3}$% or lower.

The recombinant TPL produced as described above may be utilized for the production of L-DOPA using an enzymatic process. That is, L-DOPA can be produced by allowing the obtained TPL to act on "catechol, pyruvic acid and ammonia" or "catechol and serine" to produce L-DOPA and collecting the L-DOPA. The L-DOPA-producing reaction can be performed by, for example, adding TPL to a reaction mixture containing the aforementioned substrates. TPL may be added as a crude enzyme solution. Pyruvic acid and ammonia may be contained in the reaction mixture in the form of salts, that is, pyruvate salt and ammonium salt.

Furthermore, cells of a microorganism having a gene encoding the mutant tyrosine repressor of the present invention may be directly used for the production of L-DOPA. That is, L-DOPA can be produced by allowing the microbial cells grown under a suitable culture condition to act directly on "catechol, pyruvic acid and ammonia" or "catechol and serine" to produce L-DOPA and collecting the produced L-DOPA. The microorganisms may also react with the substrates while they are growing in the medium. *Escherichia* or *Pantoea* bacteria usually require tyrosine as an inducer for expression of the TPL gene. However, in the bacteria harboring the mutant tyrosine repressor of the present invention, expression of the TPL gene is induced without addition of tyrosine to the medium. Therefore, in order to prevent contamination of tyrosine in the product, cells cultured in the absence of tyrosine are preferably used. The cells used for the production may be disrupted cells, cell fractions, or immobilized cells.

Furthermore, the mutant tyrosine repressor of the present invention and a gene encoding the repressor can be utilized for regulation of expression of a desired gene. For example, a structural gene encoding a desired protein is operably linked to a promoter of the TPL gene, and the obtained gene construct is introduced into a microorganism. Then, the mutant tyrosine repressor gene of the present invention is also transformed into the microorganism, thereby expression of the desired protein is positively regulated by the mutant tyrosine repressor. Therefore, a desired protein can be efficiently produced by culturing a microorganism which has been transformed in a medium with a mutant tyrosine repressor gene as well as a gene construct containing a structural gene of the desired protein linked to a promoter of the TPL gene. Examples of the TPL gene promoter include a sequence of nucleotide numbers 482 to 800 in SEQ ID NO: 3. The aforementioned gene construct and mutant tyrosine repressor gene may be introduced by using separate vectors, or using a single vector containing the both genes. The TPL gene may also be selected as the desired gene. In this case, TPL expression level in the host cells can be further increased, and therefore the cells can be efficiently used for production of L-DOPA.

EXAMPLES

Hereafter, the present invention will be explained more specifically by referring to the following non-limiting examples. N324D means the asparagine at position 324 has been replaced with aspartic acid. N324D mutation means a mutation causing the N324D replacement. The other replacements and mutations are designated in the same manner.

<1> Preparation of Plasmids pAH175(N324D)

Plasmid pAH175, which contains the tyrR gene having the N324D mutation, was prepared according to the scheme shown in FIG. 1. A 3.9 kb PvuII fragment of pMW118 (Nippon Gene), and a 2.4 kb SalI (blunt-ended)-SspI fragment of pTK#20 (Japanese Patent Laid-open No. 2001-238678) containing a wild-type tyrR gene of the *Pantoea agglomerans* ATCC 21434 strain were ligated to prepare pTK672. Furthermore, pTK775 (Appl. Environ. Microbiol., 66, 4764-4771 (2000)) containing a wild-type tyrR gene from the *Pantoea agglomerans* ATCC 21434 strain having the N324D mutation introduced by site-directed mutagenesis using QuikChange Kit (Stratagene), resulting in the plasmid pTK1108. Then, a 4.7 kb fragment obtained by digesting the aforementioned pTK672 with EcoRI, and a 1.6 kb fragment obtained by digesting the aforementioned pTK1108 with EcoRI were ligated to obtain pAH160. Since *Pantoea agglomerans* is ampicillin-resistant, ampicillin cannot be used as a selection marker. Accordingly, a tetracycline-resistance gene derived from pBR322 (blunt-ended 1.6 kb SspI-PpuMI fragment) was inserted into pAH160 at the ScaI site, and thereby, the plasmid pAH175 was obtained.

(ii) pAH176 (V67A, Y72C, E201G, N324D)

Figure 2:
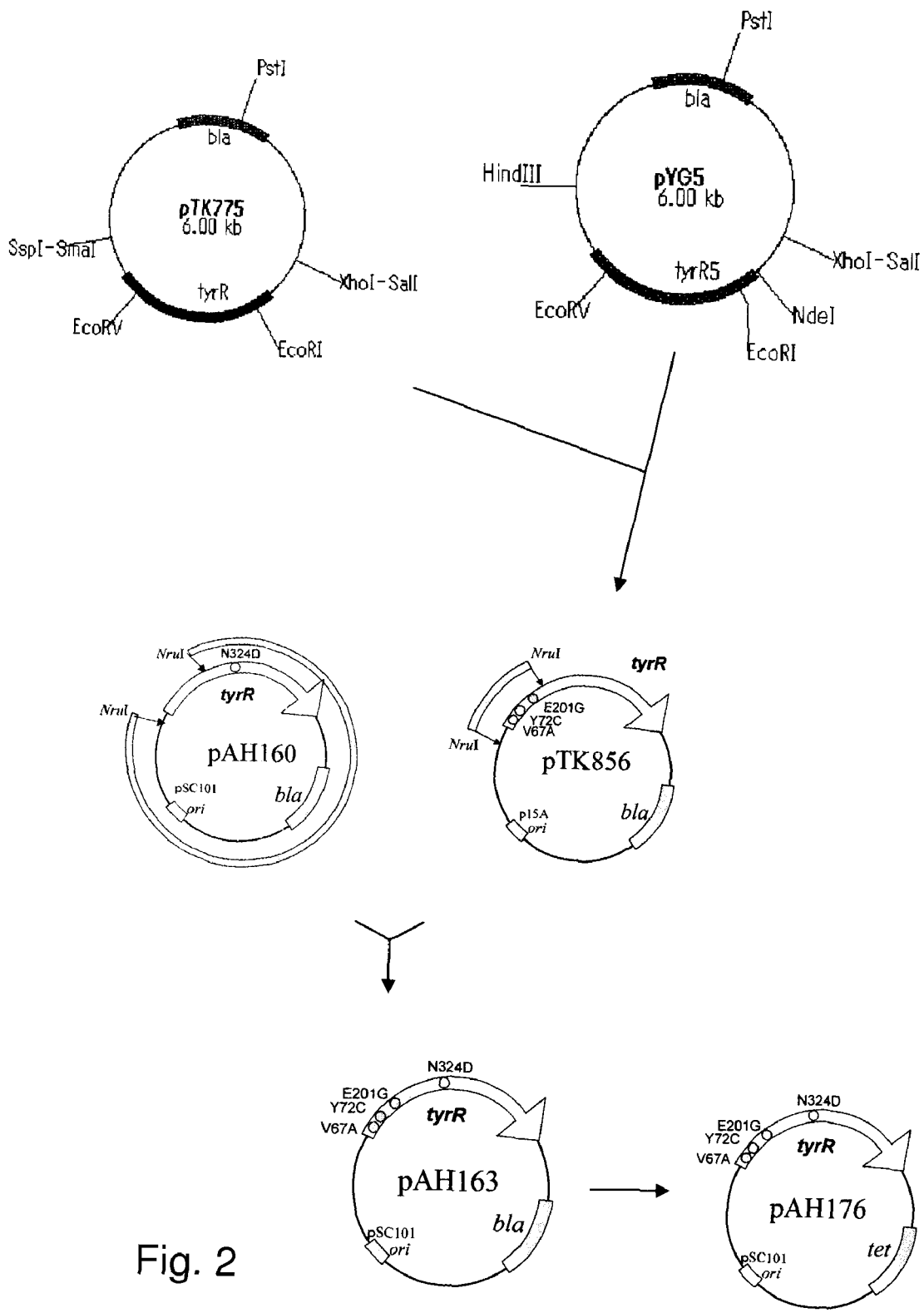
FIG. 2 shows the construction procedure for the plasmid pAH176.

Plasmid pAH176, which contains the tyrR gene having the V67A, Y72C, E201G and N324D mutations, was prepared according to the scheme shown in FIG. 2. Three of the fragments including a PstI-EcoRI fragment (2.3 kb) of pTK775, a PstI-EcoRV fragment (2.6 kb) of pTK775, and an EcoRI-EcoRV fragment (1.1 kb) of pYG5 (pACYC177 having the tyrR5 gene—a mutant-tyrR gene including the V67A, Y72C, E201G mutations—disclosed in Japanese Patent Laid-open No. 2001-238678), were ligated to prepare pTK856. Then, a 5.6 kb fragment obtained by digesting the aforementioned pAH160 with NruI and a 0.7 kb fragment obtained by digesting the aforementioned pTK856 with NruI were ligated to obtain pAH163. Furthermore, a tetracycline-resistance gene was inserted in the same manner as in the above (i), and thereby, the plasmid pAH176 was obtained.

(iii) pAH178 (V67A, Y72C, E201G, N324D, A503T)

Figure 3:
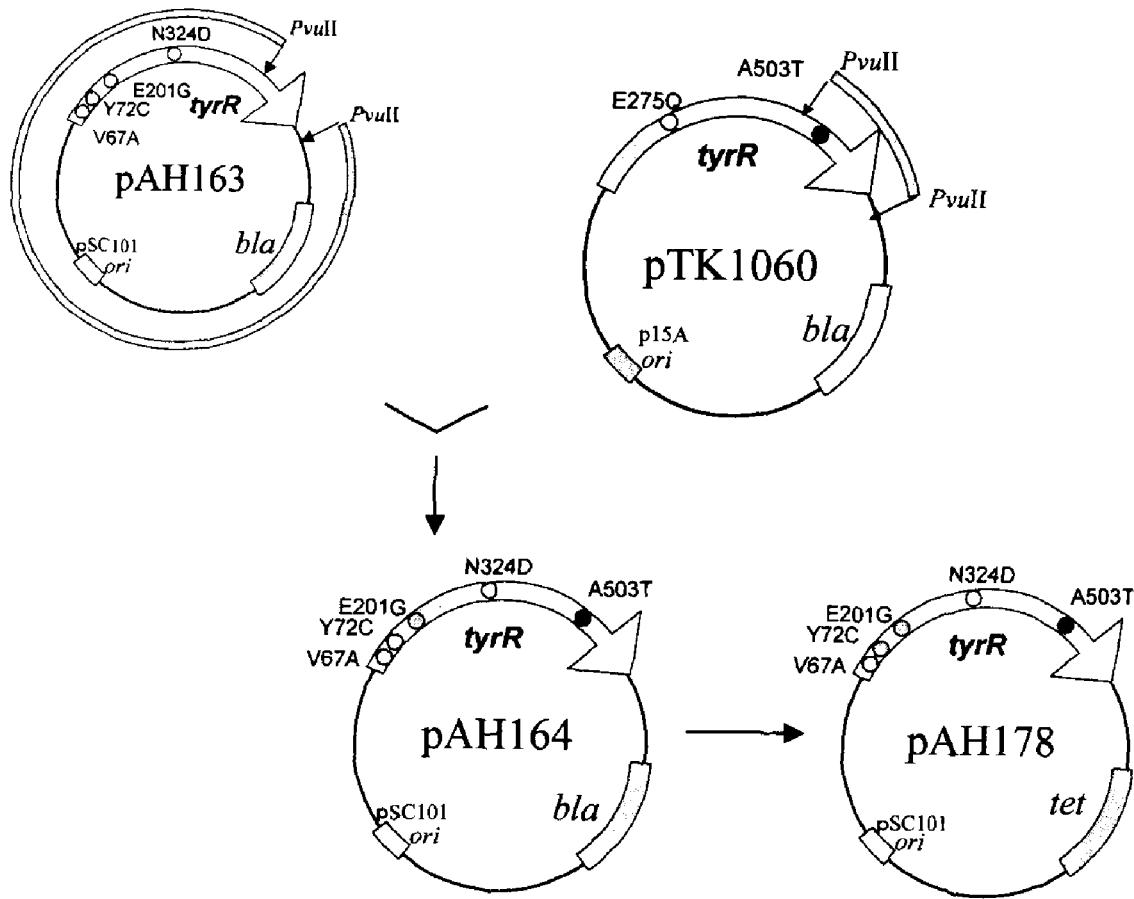
FIG. 3 shows the construction procedure for the plasmid pAH178.

Plasmid pAH178, which contains the tyrR gene having the V67A, Y72C, E201G, N324D, and A503T mutations, was prepared according to the scheme shown in FIG. 3. The E275Q mutation was introduced into pTK775 by site-directed mutagenesis to prepare pTK815. tyrR gene fragments amplified by error-prone PCR using the above pTK815 as a template was introduced into pTK774, and clones with an ability to induce increased TPL expression were selected. One of the clones was designated pTK1060, which has the A503T mutation.

The method for constructing a DNA library using pTK774 is described in the aforementioned Appl. Environ. Microbiol., 66, 4764-4771 (2000), Materials and Methods, "the section of random mutagenesis of the tyrR gene using error-prone PCR." The method for performing error-prone PCR is disclosed in Japanese Patent Laid-open No. 2001-238678. Then, a 5.9 kb fragment obtained by digesting the aforementioned pAH163 with PvuII and a 0.4 kb fragment obtained by digesting the aforementioned pTK1060 with PvuII were ligated to obtain pAH164. Furthermore, a tetracycline-resistance gene was inserted in the same manner as in (i), and thereby, the plasmid pAH178 was obtained.

(iv) pAH170 (A503T)

Figure 4:
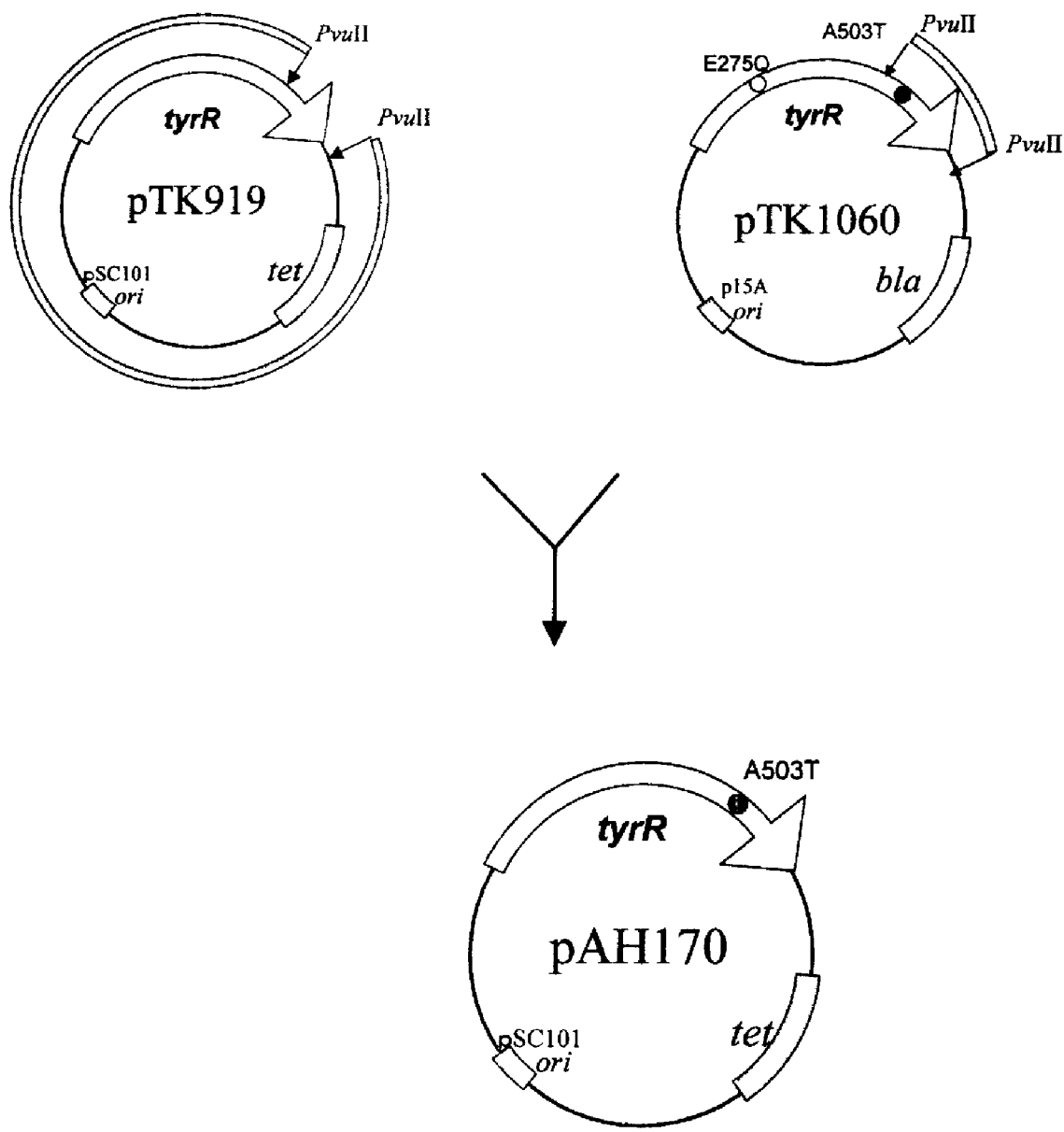
FIG. 4 shows the construction procedure for the plasmid pAH170.

Plasmid pAH170, which contains the tyrR gene having the A503T mutation, was prepared according to the scheme shown in FIG. 4. A 7.3 kb fragment obtained by digesting pTK919 (Japanese Patent Laid-open No. 2001-238678) with PvuII and a 0.4 kb fragment obtained by digesting the aforementioned pTK1060 with PvuII were ligated, and thereby, the plasmid pAH170 was obtained.

(V) pAH172 (V67A, Y72C, E201G, A503T)

Figure 5:
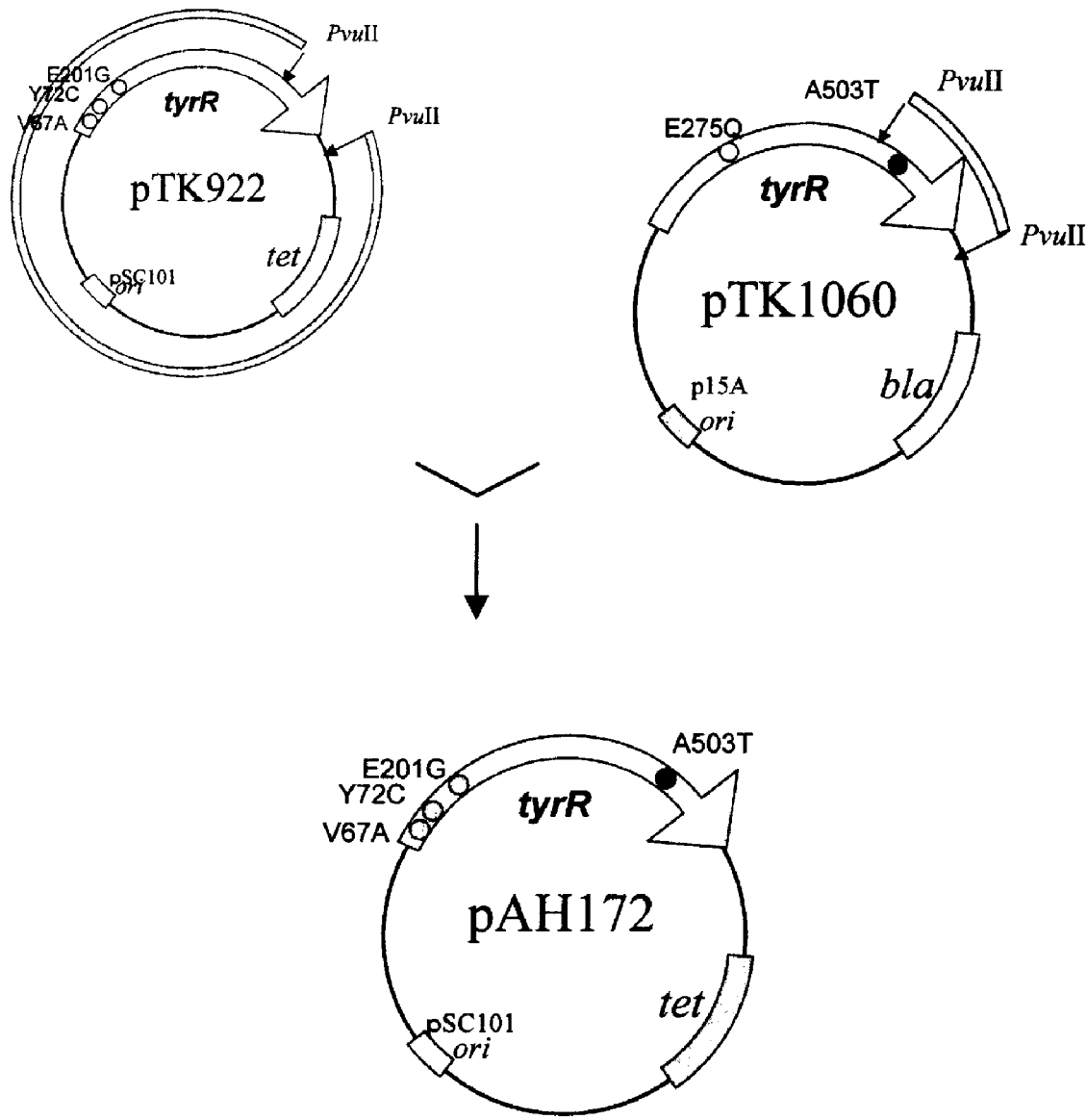
FIG. 5 shows the construction procedure for the plasmid pAH172.

Plasmid pAH172, which contains the tyrR gene having the V67A, Y72C, E201G and A503T mutations, was prepared according to the scheme shown in FIG. 5. A 7.3 kb fragment obtained by digesting pTK922 (Japanese Patent Laid-open No. 2001-238678) with PvuII and a 0.4 kb fragment obtained by digesting the aforementioned pTK1060 with PvuII were ligated, and thereby, the plasmid pAH172 was obtained.

(vi) pAH177 (N324D, A503T)

Figure 6:
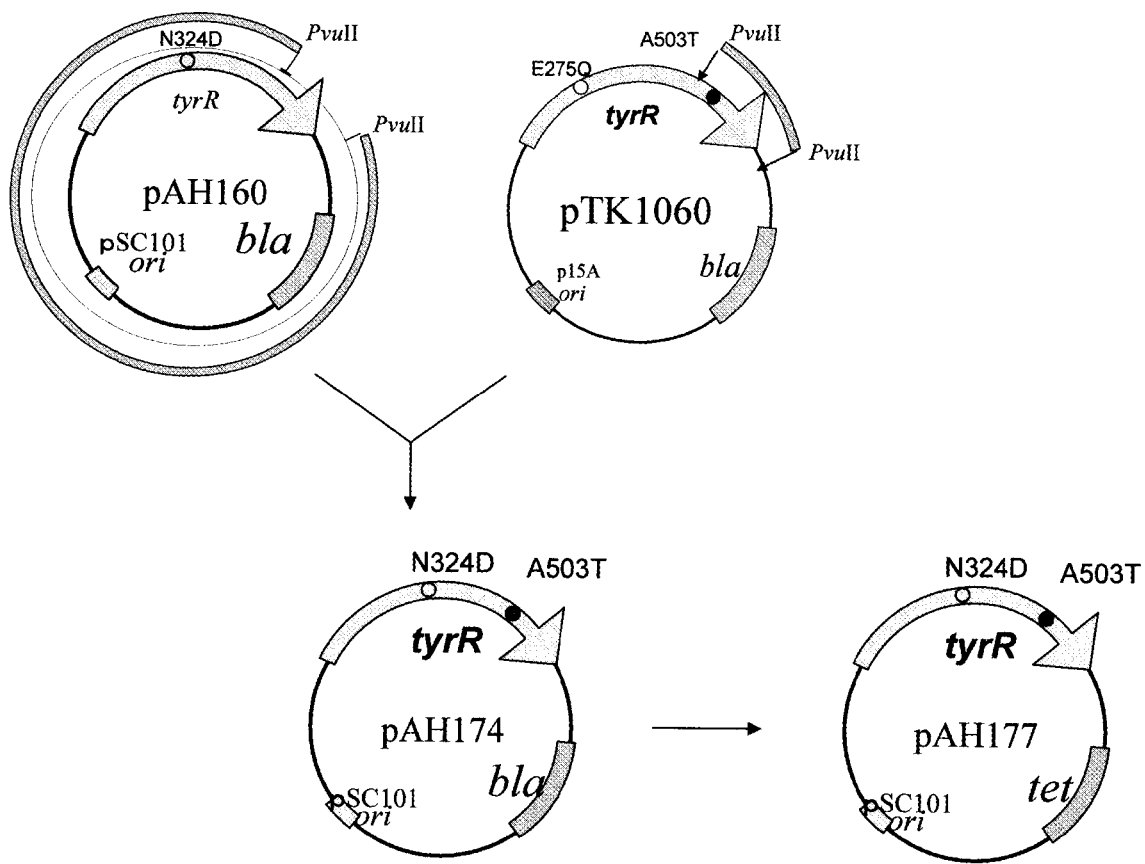
FIG. 6 shows the construction procedure for the plasmid pAH177.

Plasmid pAH177, which contains the tyrR gene having the N324D and A503T mutations, was prepared according to the scheme shown in FIG. 6. A 7.3 kb fragment obtained by digesting the aforementioned pAH160 with PvuII and a 0.4 kb fragment obtained by digesting the aforementioned pTK1060 with PvuII were ligated, and thereby, the plasmid pAH177 was obtained.

<2> Introduction of Wild-Type or Mutant tyrR Gene into *Pantoea agglomerans*

The plasmids obtained in the above (i) to (vi), pTK922 containing the tyrR gene having the V67A, Y72C, E201G mutations, and pTK919 containing a wild-type tyrR gene, were respectively introduced into the YG17 strain by the heat shock method (Japanese Patent Laid-open No. 2001-238678). The YG17 strain is a tyrR gene-disrupted strain of *Pantoea agglomerans* (*Erwinia herbicola*). That is, 200 μL of competent cells was added to 20 μL of a solution containing each of the aforementioned plasmids, placed on ice for 30 minutes and heated to 42° C. for 30 seconds. The cells were added to 800 μL of SOB medium, incubated at 37° C. for 1 hour, then applied to a plate and cultured overnight at 30° C. The strains obtained by this procedure are shown in Table 1. In Table 1, the V67A, Y72C, and E201G mutations are designated as NT, the N324D mutation as Cen, and the A503T mutation as CT.

TABLE 1

Amino acid substitutions contained in each mutant tyrR gene

| Strain | Introduced plasmid | Abbreviation | | Amino acid replacements in each strain | | | | |
|---|---|---|---|---|---|---|---|---|
| | | | | V67A | Y72C | E201G | N324D | A503T |
| YG40 | pTK922 | NT | | ○ | ○ | ○ | | |
| AH179 | pAH175 | | Cen | | | | ○ | |
| AH180 | pAH170 | | | CT | | | | ○ |
| AH181 | pAH176 | NT | Cen | ○ | ○ | ○ | ○ | |
| AH182 | pAH177 | | Cen | CT | | | ○ | ○ |
| AH183 | pAH172 | NT | | CT | ○ | ○ | ○ | ○ |
| AH184 | pAH178 | NT | Cen | CT | ○ | ○ | ○ | ○ | ○ |
| YG38 | pTK919 | | | | | Wild-type | | |

<3> Evaluation of TPL Activity of Each Mutant tyrR Gene-Introduced Strains

These strains and a wild-type strain AJ2985 (ATCC 21434) were each cultured in 100 mL of a medium in the presence or absence of 0.2% tyrosine at 28° C. for 28, 32 or 36 hours with shaking. The composition of the medium is shown in Table 2.

TABLE 2

| Composition of the medium used for TPL expression | |
|---|---|
| $KH_2PO_4$ | 0.20% |
| $MgSO_4·7H_2O$ | 0.10% |
| $FeSO_4·7H_2O$ | 0.0010% |
| Pyridoxine hydrochloride | 0.010% |
| Glycerol | 0.60% |
| Succinic acid | 0.50% |
| L-Methionine | 0.10% |
| L-Alanine | 0.20% |
| Glycine | 0.050% |
| L-Phenylalanine | 0.10% |
| Soybean protein hydrolysate | 1.5% |
| L-Tyrosine (added only to tyrosine added medium) | 0.20% | pH 7.0 (adjusted with KOH)

COMPOUND-F (Ajinomoto Co., Inc.) was used as the soybean protein hydrolysate. The tyrosine content in this product is estimated to be 1.5±0.15% on the basis of the amino acid composition of the product. Therefore, even when tyrosine was not added, a trace amount ($2.25 \times 10^{-3}$%) of tyrosine is in the medium. However, the presence of tyrosine in such an amount does not cause a substantial problem in the production of L-DOPA by fermentation.

After completion of the culture, the cells were suspended in 10 mM potassium phosphate buffer (pH 7.0) containing 0.2 mM pridoxal-5'-phosphate (PLP), 5 mM 2-mercaptoethanol, and 4 mM EDTA (pH 7.0), and disrupted by ultrasonication. The disrupted cell suspension was dialyzed against a large volume of the aforementioned buffer overnight, and the enzyme solution was thereby prepared. Then, the amount of protein and TPL activity in the enzyme solution were determined.

Figure 7:
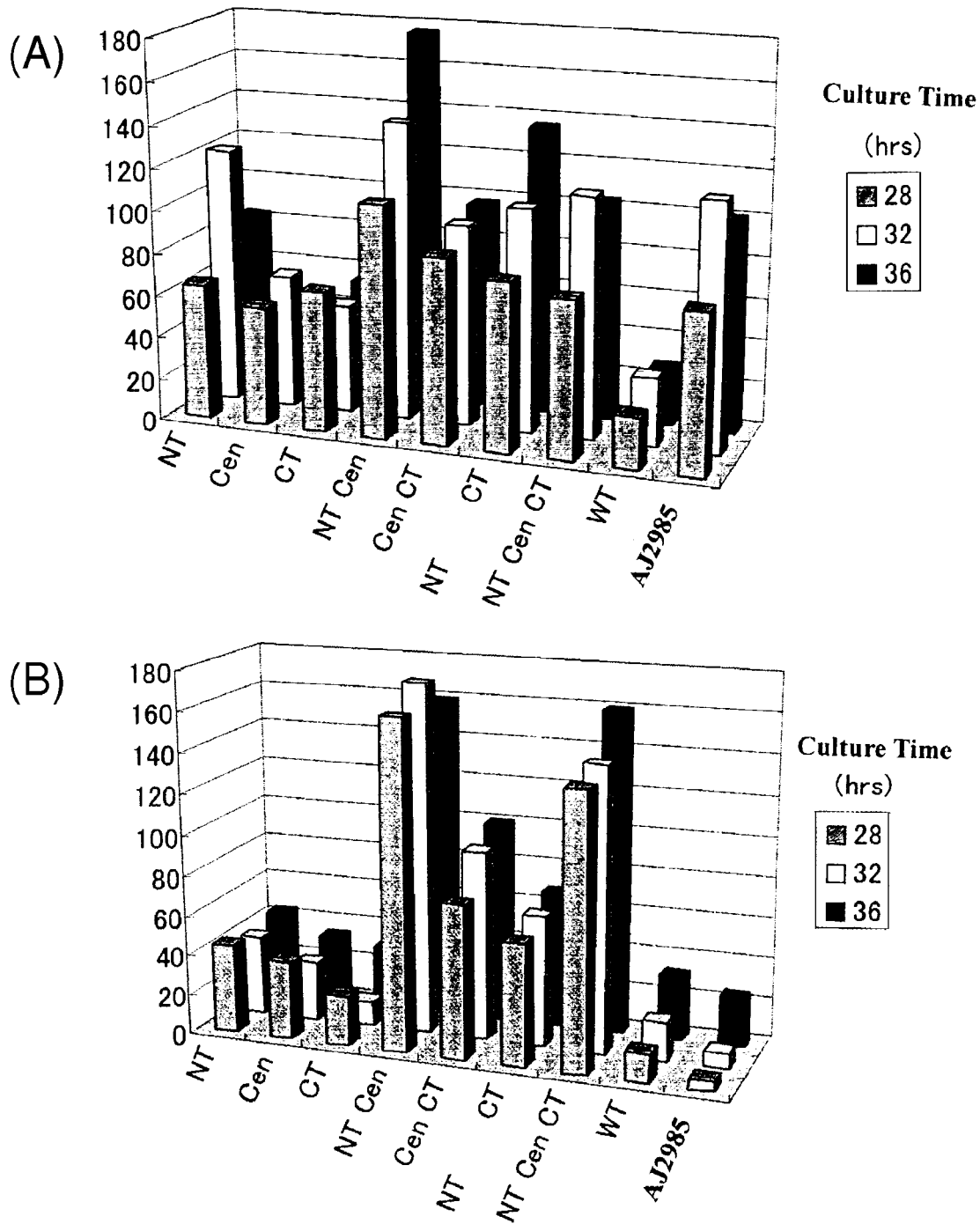
FIG. 7 shows TPL activity per unit cell weight of the strains transformed with a wild-type or mutant tyrR gene in the presence (A) or absence (B) of tyrosine.

The quantification of protein was performed by the Lowry method (Lowry, O. H. et al., J. Biol. Chem., 193, 265 (1951)) using bovine serum albumin as a standard. The TPL activity was determined as follows by using chemically synthesized S-o-nitrophenyl-L-cysteine (SOPC) as a substrate. That is, a reaction solution containing 0.2 mM SOPC, 0.1 mM PLP, 5 mM 2-mercaptoethanol, and 100 mM potassium phosphate buffer (pH 8.0) was preincubated in a water bath at 30° C. for 4 minutes. Then, 1 mL of this reaction solution was mixed with 50 μL of the aforementioned enzyme solution. Since SOPC shows maximum absorption at 368 nm, reduction in absorbance at 370 nm was measured ($\epsilon=1,860$). The amount of enzyme consuming 1 μmole of SOPC per 1 minute was defined as 1 unit. The TPL activity per unit cell weight for each strain relative to the TPL activity per unit cell weight for the wild-type strain cultured in the presence of tyrosine for 36 hours, which was taken as 100, are shown in Table 3 and FIG. 7.

TABLE 3

Activity per unit cell weight

| With addition of tyrosine | 28 hrs | 32 hrs | 36 hrs | Without addition of tyrosine | 28 hrs | 32 hrs | 36 hrs |
|---|---|---|---|---|---|---|---|
| YG40 (NT) | 65 | 122 | 83 | YG40 (NT) | 45 | 40 | 44 |
| AH179 (Cen) | 57 | 63 | 42 | AH179 (Cen) | 39 | 30 | 34 |
| AH180 (CT) | 67 | 52 | 55 | AH180 (CT) | 25 | 12 | 31 |
| AH181 (NT Cen) | 110 | 140 | 176 | AH181 (NT Cen) | 162 | 173 | 159 |
| AH182 (Cen CT) | 89 | 95 | 98 | AH182 (Cen CT) | 76 | 94 | 100 |
| AH183 (NT CT) | 80 | 106 | 136 | AH183 (NT CT) | 60 | 65 | 68 |
| AH184 (NT Cen CT) | 75 | 114 | 104 | AH184 (NT Cen CT) | 136 | 140 | 160 |
| YG38 (WT) | 25 | 33 | 28 | YG38 (WT) | 14 | 19 | 32 |
| Wild-type strain AJ2985 | 76 | 117 | 100 | Wild-type strain AJ2985 | 5 | 8 | 24 |

When tyrosine was added, the AH181 (NT Cen), AH182 (Cen CT), AH183 (NT CT), and AH184 (NT Cen CT) strains showed a TPL activity comparable to or higher than that of the wild-type strain (AJ2985).

When tyrosine was not added, the AH181 (NT Cen), AH182 (Cen CT), AH183 (NT CT) and AH184 (NT Cen CT) strains showed a TPL activity 10 times higher or more than that of the wild-type strain, which hardly induced TPL activity. From these results, it was found that *Pantoea agglomerans* transformed with the aforementioned mutant tyrR gene could express a large amount of TPL even when tyrosine was not added to the medium.

SOPC used for the measurement of TPL activity was chemically synthesized and purified by the following procedure:

(1) 100 mL of 10 mM cysteine (dissolved in water) was mixed with 100 mL of 10 mM o-DNB (dissolved in EtOH).

(2) 3 drops of 28% aqueous ammonia was added to the above mixture and incubated overnight at 50° C.

(3) Evaporation was performed at 50° C. to obtain crystals of o-DNB.

(4) Centrifugation was performed at 3,500 rpm at room temperature for 3 minutes to remove the crystals.

(5) Paper chromatography was performed overnight (developing solution of 1-butanol:water:acetic acid at the ratio of 4:1:1).

(6) Paper was dried, and then the portion showing UV absorption was excised and cut into pieces, and immersed in water to perform extraction overnight.

(7) The solution was filtered by using a nitrocellulose filter (pore size: 5.0 μm).

(8) Evaporation was performed at 50° C. again.

(9) The resulting product was lyophilized, and thereby, SOPC powder was obtained.

<4> Production of L-DOPA Using Mutant tyrR Gene-Introduced Strains

The following 5 strains were used for L-DOPA production:

Control strain (pTK631/AJ2985ΔtyrR::kan+)

YG38 strain (tyrR+/AJ2985ΔtyrR::kan+)

YG40 strain (tyrR+NT/AJ2985ΔtyrR::kan+)

AH181 strain (tyrR+NT+Cen/AJ2985ΔtyrR::kan+)

AH184 strain (tyrR+NT+Cen+CT/AJ2985ΔtyrR::kan+)

The vector pTK631 used in the control strain is described in Applied and Environmental Microbiology, Vol. 66, pp. 4764-4771 (2000).

First, each of the aforementioned strains was cultured on a refresh slant (basal medium added with 2% of agar and adjusted to pH 7.5 at 31.5° C. for 24 hours. One loop of cells grown on the refresh slant were inoculated into 100 mL of the aforementioned medium with or without addition of 0.2% tyrosine in a 500-mL Sakaguchi flask, and cultured at 28° C. for 17 hours with shaking at 140 rpm. Growth of all the strains on the slant was not very different when compared with each other.

After completion of the culture, 5 mL of the culture was centrifuged (3000 rpm, 15 minutes) to collect the cells. The obtained cells were suspended in 5 mL of a substrate solution having the following composition and reacted at 15° C. for 1 hour.

| <Substrate solution for determining TPL activity> | |
|---|---|
| Sodium pyruvate | 1.55 g/dl |
| Catechol | 1.0 g/dl |
| Ammonium chloride | 4.7 g/dl |
| Ammonium nitrate | 0.13 g/dl |
| Sodium sulfite | 0.27 g/dl |
| EDTA-2Na | 0.4 g/dl | pH 8.0 (adjusted with aqueous ammonia immediately before the reaction)

After completion of the reaction, the reaction mixture was adjusted to a pH below 1.0 with hydrochloric acid and further diluted 100 times, and then the amount of produced L-DOPA was analyzed by HPLC. The amounts of cells and amounts of produced L-DOPA are shown in Table 4. In the column of "Tyrosine", "+" indicates addition of 0.2% tyrosine, and "−" indicates no addition of tyrosine.

TABLE 4

| Evaluated strain | Tyrosine | Amount of cells in culture (g/dl) | Amount of DOPA (g/dl) produced | DOPA-producing activity of cells (g/g/hr) |
|---|---|---|---|---|
| Control strain | + | 0.25 | 0.000 | 0.00 |
| (vector) | − | 0.31 | 0.000 | 0.00 |
| YG38 strain | + | 0.34 | 0.290 | 0.85 |
| (wild-type TyrR) | − | 0.28 | 0.076 | 0.27 |
| YG40 strain | + | 0.22 | 0.387 | 1.76 |
| (NT) | − | 0.20 | 0.210 | 1.05 |
| AH181 strain | + | 0.30 | 0.894 | 2.98 |
| (NT + Cen) | − | 0.32 | 0.677 | 2.13 |
| AH184 strain | + | 0.29 | 0.995 | 3.41 |
| (NT + Cen + CT) | − | 0.32 | 1.112 | 3.48 |

Table 4 shows that both the amount of L-DOPA produced and L-DOPA-producing activity per unit cell weight were markedly increased by introduction of the Cen mutation or Cen and CT mutations into the known mutant tyrosine repressor gene having the NT mutation described in Japanese Patent Laid-open No. 2001-238678. The strain transformed with the mutant tyrosine repressor having the NT mutation as well as the strain transformed with the wild-type tyrosine repressor required tyrosine to produce a sufficient amount of L-DOPA and to exhibit sufficient L-DOPA-producing activity. On the other hand, the amount of L-DOPA produced and L-DOPA-producing activity per unit cell weight of the strain transformed with the Cen or Cen+CT mutation(s) in combination with NT mutation (NT+Cen or NT+Cen+CT) were almost the same between the medium containing tyrosine and the medium without tyrosine, and, in particular, NT+Cen+CT strain showed a higher amount of produced L-DOPA and higher L-DOPA-producing activity per unit cell weight in the absence of tyrosine than in the presence of tyrosine. That is, although a conventional method for producing TPL used for L-DOPA production requires tyrosine to induce TPL expression, this induction by tyrosine has been made unnecessary by the present invention.

<5> Evaluation of Mutant TyrR in *Escherichia coli*

Figure 8:
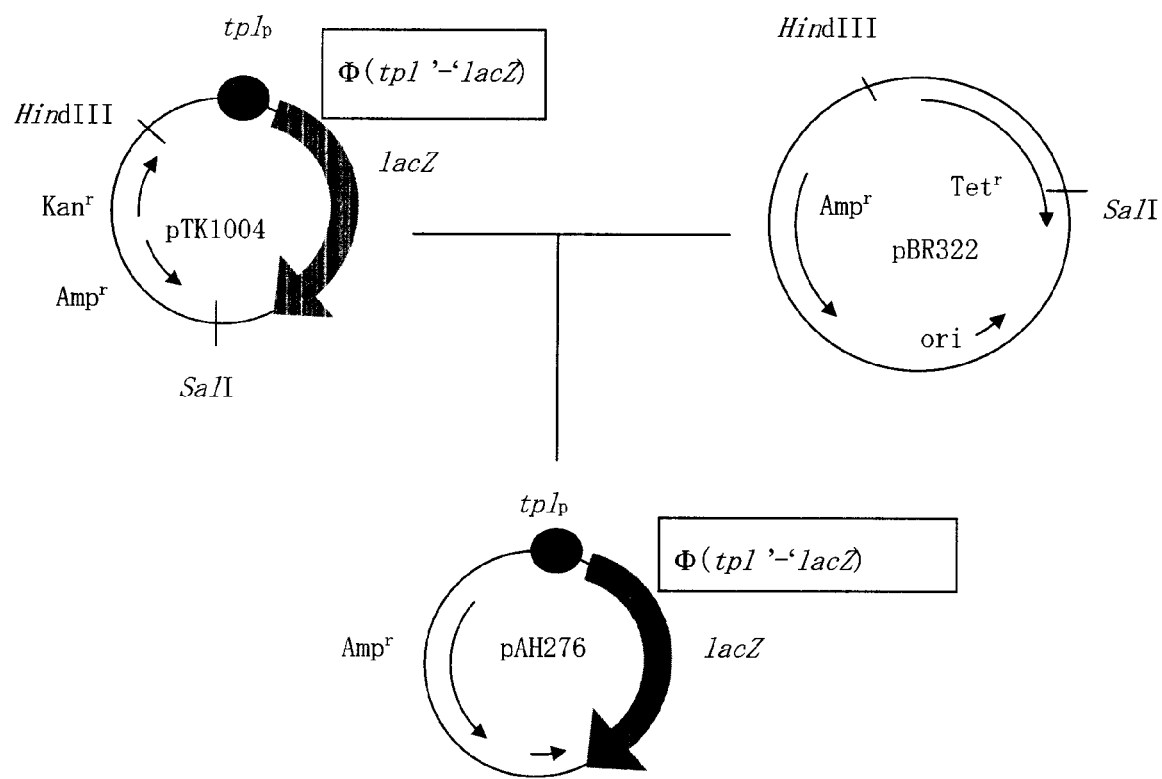
FIG. 8 shows construction of the Φ(tpl'-'lacZ) reporter plasmid.

To examine whether the mutant tyrosine repressor (TyrR) of the present invention could also activate transcription from the TPL gene promoter of *Pantoea agglomerans* in *Escherichia coli*, the following experiment was performed. First, in order to observe transcriptional activity of the mutant TyrR based on β-galactosidase activity, a reporter plasmid containing the lacZ gene encoding β-galactosidase linked to the tpl promoter of *Pantoea agglomerans* (Φ(tpl'-'lacZ) gene) was constructed. A 5.9 kb HindIII-SalI fragment containing the Φ(tpl'-'lacZ) gene was excised from pTK1004 and ligated to a fragment obtained by digesting pBR322 with HindIII and SalI, and thereby, plasmid pAH276 containing the Φ(tpl'-'lacZ) gene as shown in FIG. 8 was obtained.

The aforementioned pTK1004 was prepared as follows. First, an 8.6 kb SacI-SacII fragment excised from pTK312 (Japanese Patent Laid-open No. 2001-238678) and blunt-ended, and a 1.1 kb SacI-BamHI fragment excised from pMC1871 (Pharmacia) and blunt-ended were ligated to obtain pTK1003. Then, a 0.5 kb XmnI fragment excised from pTrc99A (Pharmacia) was inserted into pTK1003 at the NcoI site (blunt-ended) to obtain pTK1004.

An *Escherichia coli* ΔtyrRΔlac strain, TK743, deficient in endogenous tyrR gene and lacZ gene, was transformed with each of the 4 kinds of the plasmids, i.e., a control plasmid pTK631, pTK919 containing a wild-type tyrR gene, pTK922 containing the tyrR (V67A Y72C E201G) gene, and pAH178 containing the tyrR (V67A Y72C E201G N324D A503T) gene. The obtained transformants were further transformed with the aforementioned Φ(tpl'-'lacZ) reporter plasmid pAH276. The obtained strains were precultured in LB medium, LB medium containing 1 mM tyrosine and LB medium containing 1 mM phenylalanine overnight at 37° C., respectively. Then, the culture was collected and inoculated into 100-fold volume of a main culture medium, and the main culture was performed in each fresh medium at 37° C. Then, the β-galactosidase activity was determined when $OD_{600}$ reached 0.5.

Figure 9:
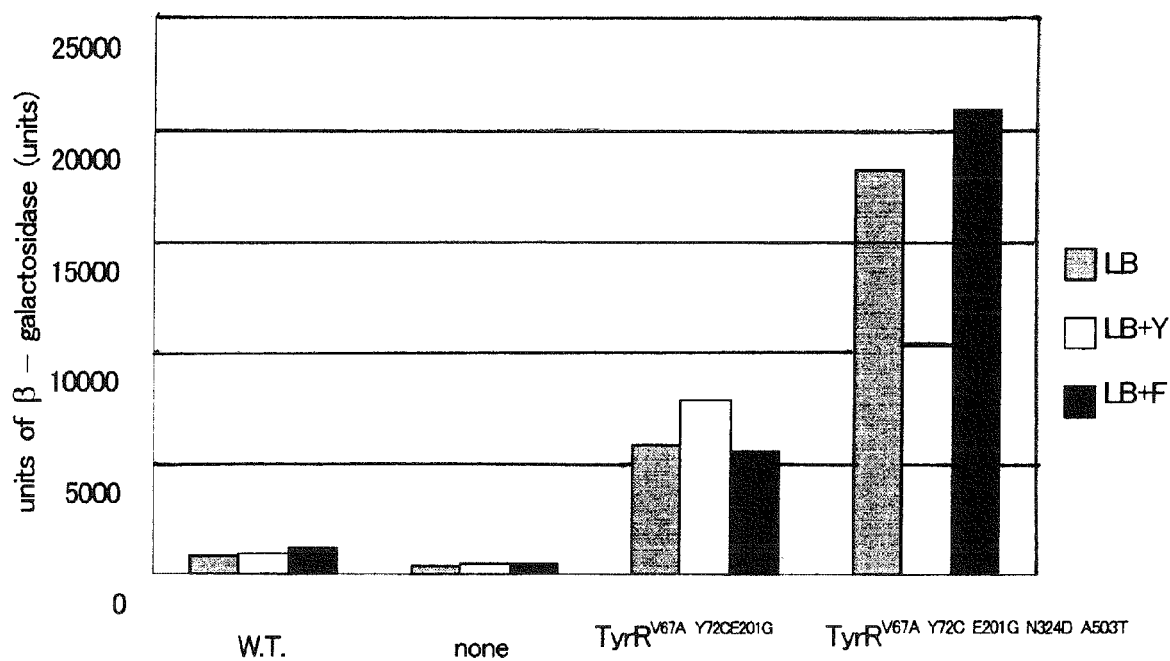
FIG. 9 shows ability of mutant TyrR to activate transcription of Φ(tpl'-'lacZ). LB+Y denotes tyrosine-added LB medium, and LB+F denotes phenylalanine-added LB medium.

As shown in FIG. 9, in the LB medium without tyrosine, the strain containing TyrR (V67A Y72C E201G) showed β-galactosidase activity about 7 times higher than that of the strain containing the wild-type TyrR, and the strain containing TyrR (V67A Y72C E201G N324D A503T) showed β-galactosidase activity about 22 times higher than that of the strain containing the wild-type TyrR. Furthermore, these strains showed β-galactosidase activity about 8 times or 10 times higher than the strain containing the wild-type TyrR in the LB medium added with 1 mM phenylalanine, and showed β-galactosidase activity about 4.5 times or 17 times higher than the strain containing the wild-type TyrR in the LB medium added with 1 mM tyrosine. Induction by tyrosine or phenylalanine was hardly observed in the strain containing the wild-type TyrR, which was maybe because the LB medium originally contained large amounts of these aromatic amino acids. From these results, it was revealed that the mutant TyrR increased transcription from the tpl promoter even in *Escherichia coli* in the absence of tyrosine.

INDUSTRIAL APPLICABILITY

L-DOPA is useful in the treatment of Parkinson's disease or the like, and can be efficiently produced using recombinant TPL or a microorganism expressing high amounts of TPL obtained using the mutant tyrosine repressor of the present invention.

While the invention has been described in detail with reference to preferred embodiments thereof, it will be apparent to one skilled in the art that various changes can be made, and equivalents employed, without departing from the scope of the invention. Each of the aforementioned documents, as well as the foreign priority document, JP 2004-095147, is incorporated by reference herein in its entirety.

---

We claim:

1. A DNA encoding a mutant tyrosine repressor which comprises mutations at positions selected from the group consisting of:
   (a) position 67, position 72, position 201, and position 503;
   (b) position 324 and position 503;
   (c) position 67, position 72, position 201, position 324, and position 503; and
   (d) position 67, position 72, position 201, and position 324, wherein said positions are as shown in SEQ ID NO: 2, and wherein said DNA hybridizes under stringent conditions to the complement to a polynucleotide having nucleotides 442 to 2004 in SEQ ID NO: 1, and wherein said stringent conditions comprise washing in 0.1×SSC and 0.1% SDS at 65° C.

2. The DNA of claim 1, wherein said repressor does not require tyrosine to induce expression of a tyrosine phenol-lyase gene.

3. The DNA according to claim 1, wherein said mutation at position 67 is an alanine, said mutation at position 72 is a cysteine, said mutation at position 201 is a glycine, said mutation at position 324 is an aspartic acid, and said mutation at position 503 is a threonine.

4. The DNA according to claim 1, wherein said mutant tyrosine repressor includes substitution, deletion, insertion, addition or inversion of one to 20 amino acid residues at a position other than the positions listed in (a), (b), or (c), and wherein said mutant tyrosine repressor does not require tyrosine to induce expression of a tyrosine phenol-lyase gene.

5. The DNA according to claim 1, wherein said repressor originates from *Pantoea agglomerans* prior to mutation.

6. The DNA according to claim 5, wherein said repressor comprises the amino acid sequence of SEQ ID NO: 2 prior to mutation.

7. An *Escherichia* or *Pantoea* bacterium which is transformed with said DNA according to claim 1.

8. The *Escherichia* or *Pantoea* bacterium according to claim 7, further comprising a tyrosine phenol-lyase structural gene operably linked to a tyrosine phenol-lyase gene promoter.

9. A method for producing L-3,4-dihydroxyphenylalanine comprising
   (a) allowing said *Escherichia* or *Pantoea* bacterium according to claim 7 to act on a mixture selected from the group consisting of
      (1) catechol, pyruvic acid and ammonia, and
      (2) catechol and serine, and
   (b) collecting said L-3,4-dihydroxyphenylalanine.

10. The method for producing L-3,4-dihydroxyphenylalanine according to claim 9, wherein said bacterium is grown in the absence of tyrosine.

11. A DNA encoding a mutant tyrosine repressor which does not require tyrosine to induce expression of a tyrosine phenol-lyase gene, comprising mutations at positions selected from the group consisting of:
   (a) position 67, position 72, position 201, and position 503;
   (b) position 324 and position 503;

(c) position 67, position 72, position 201, position 324, and position 503; and (d) position 67, position 72, position 201, and position 324, wherein said positions represent the positions in the amino acid sequence of SEQ ID NO: 2, and wherein said mutant tyrosine repressor has a homology of 95% or more to the amino acid sequence of SEQ ID NO: 2.

12. The DNA of claim 11, wherein said mutation at position 67 is an alanine, said mutation at position 72 is a cysteine, said mutation at position 201 is a glycine, said mutation at position 324 is an aspartic acid, and said mutation at position 503 is a threonine.

13. An *Escherichia* or *Pantoea* bacterium which is transformed with said DNA according to claim 11.

14. The *Escherichia* or *Pantoea* bacterium according to claim 13, further comprising a tyrosine phenol-lyase structural gene operably linked to a tyrosine phenol-lyase gene promoter.

15. A method for producing L-3,4-dihydroxyphenylalanine comprising
  (a) allowing said *Escherichia* or *Pantoea* bacterium according to claim 13 to act on a mixture selected from the group consisting of
    (1) catechol, pyruvic acid, and ammonia, and
    (2) catechol and serine, and
  (b) collecting said L-3,4-dihydroxyphenylalanine.

16. The method for producing L-3,4-dihydroxyphenylalanine according to claim 15, wherein said bacterium is grown in the absence of tyrosine.

* * * * *